(12) United States Patent
Ogletree

(10) Patent No.: US 6,509,348 B1
(45) Date of Patent: Jan. 21, 2003

(54) COMBINATION OF AN ADP-RECEPTOR BLOCKING ANTIPLATELET DRUG AND A THROMBOXANE $A_2$ RECEPTOR ANTAGONIST AND A METHOD FOR INHIBITING THROMBUS FORMATION EMPLOYING SUCH COMBINATION

(75) Inventor: Martin L. Ogletree, Newtown, PA (US)

(73) Assignee: Bristol-Myers Squibb Company, Princeton, NJ (US)

(*) Notice: Subject to any disclaimer, the term of this patent is extended or adjusted under 35 U.S.C. 154(b) by 0 days.

(21) Appl. No.: 09/428,611

(22) Filed: Oct. 27, 1999

Related U.S. Application Data

(60) Provisional application No. 60/106,813, filed on Nov. 3, 1998.

(51) Int. Cl.[7] .......................... A61K 31/44; A61K 31/42; A61K 31/41; A61K 31/55
(52) U.S. Cl. .......................... 514/301; 514/374; 514/212; 514/365
(58) Field of Search ................................. 514/301, 212, 514/326, 365, 374, 381

(56) References Cited

U.S. PATENT DOCUMENTS

| | | |
|---|---|---|
| 4,591,592 A | 5/1986 | Chowhan |
| 5,288,726 A | 2/1994 | Koike et al. |
| 5,312,818 A | 5/1994 | Rubin et al. |
| 5,576,328 A | 11/1996 | Herbert et al. |
| 5,800,385 A * | 9/1998 | Demopulos et al. ........... 604/49 |

FOREIGN PATENT DOCUMENTS

WO     WO 97/29753     8/1997

OTHER PUBLICATIONS

Yao et al, 1992, Circ. Res., 70(1), 39–48.*
Hirata et al, 1995, Jpn. J. Pharmacol., 67(1), 51–7.*
Gomoll et al, 1994, Eur. J. Pharmacol., 271(2/3), 471–9.*
Umemura et al, 1995, Jpn. J. Pharmacol., 67(3), 253–8.*
"Superior activity of a thromboxane receptor antagonits as compared with aspirin in rat models of arterial and venous thrombosis", Schumacher et al, Journal of Cardiovascular Pharmacology, 1993, 22 (4) 526–33.*
"Ferret model of electrical–induction of arterial thrombosis that is sensitive to aspirin", Schumacher et al., 1986, Journal of Pharmacological and Toxicological methods, 35(1) 3–10.*
Gomoll et al, 1994, J. Cardiovasc. Pharmacol., 24(6), 960–8.*

* cited by examiner

*Primary Examiner*—Zohreh Fay
*Assistant Examiner*—Brian-Yong Kwon
(74) *Attorney, Agent, or Firm*—Burton Rodney

(57) ABSTRACT

A method is provided for inhibiting platelet aggregation and thrombus formation by administering to a patient an ADP-receptor blocking antiplatelet drug, such as clopidogrel, in combination with a thromboxane $A_2$ receptor antagonist, such as ifetroban, and optionally a cholesterol lowering drug, such as an HMG CoA reductase inhibitor, for example, pravastatin.

3 Claims, No Drawings

COMBINATION OF AN ADP-RECEPTOR BLOCKING ANTIPLATELET DRUG AND A THROMBOXANE A₂ RECEPTOR ANTAGONIST AND A METHOD FOR INHIBITING THROMBUS FORMATION EMPLOYING SUCH COMBINATION

This application claims the benefit of Provisional application No. 60/106,813, filed Nov. 3, 1998.

FIELD OF THE INVENTION

The present invention relates to a novel combination of an ADP-receptor blocking antiplatelet drug, such as clopidogrel, and a thromboxane $A_2$ receptor antagonist such as ifetroban, and optionally a cholesterol lowering drug, such as pravastatin, and to a method for inhibiting platelet aggregation and thrombus formation employing such combination.

BACKGROUND OF THE INVENTION

Clopidogrel is a thieno-[3,2-c]pyridine derivative which has the chemical name methyl (4)-(S)-α-(o-chlorophenyl)-6,7-dihydrothieno[3,2-c]pyridine-5-acetate and the formula

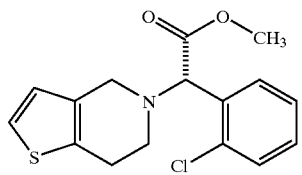

including pharmaceutically acceptable acid addition salts thereof, preferably the hydrogen sulfate salt, and is disclosed in U.S. Pat. No. 4,529,596 to Aubert et al and U.S. Pat. No. 4,847,265 to Badorc et al as having blood platelet aggregation inhibiting activity and anti-thrombotic activity and thus useful in inhibiting or preventing arterial and venous thrombosis.

U.S. Pat. No. 5,576,328 to Herbert et al discloses that clopidogrel may be employed in secondary prevention of ischemic events such as myocardial infarction, unstable or stable angina, acute reocclusion after percutaneous transluminal coronary angioplasty (PTCA), restenosis after PTCA, thrombotic stroke, transient ischemic attack, reversible ischemic neurological deficit, and intermittent claudication.

The above patents are incorporated herein by reference.

WO 97/29753 published Aug. 21, 1997, discloses a pharmaceutical composition containing clopidogrel and aspirin.

Ticlopidine hydrochloride is disclosed in U.S. Pat. No. 4,591,592 as a platelet aggregation inhibitor and is marketed in the U.S. under the name Ticlid™ by Roche Laboratories and has the chemical name 5-[(2-chlorophenyl)methyl]-4,5,6,7-tetrahydrothieno[3,2-c]pyridine hydrochloride and the structure

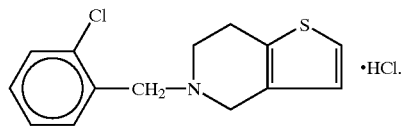

U.S. Pat. No. 5,288,726 (assigned to Sankyo) discloses a platelet aggregation inhibitor CS-747 which has the structure and name as follows:

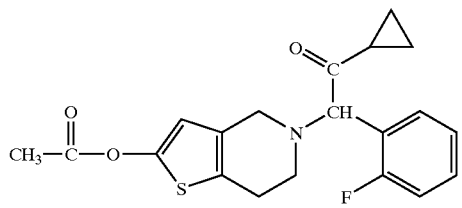

2-acetoxy-5-(α-cyclopropylcarbonyl-2-fluorobenzyl)-4,5,6,7-tetrahydrothieno[3,2-c]pyridine.

U.S. Pat. No. 5,100,889 to Misra et al discloses 7-oxabicycloheptyl substituted heterocyclic amide prostacyclin analogs which are potent thromboxane $A_2$ receptor antagonists and thus are useful in inhibiting platelet aggregation and thrombus formation. The Misra et al compounds have the structure

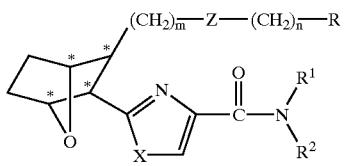

and including all stereoisomers thereof, wherein m is 1, 2 or 3; n is 0, 1, 2, 3 or 4;

Z is —(CH₂)₂—, —CH=CH— or

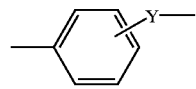

wherein Y is O, a single bond or vinyl (—CH=CH—), with the provisos that when n is 0, if Z is

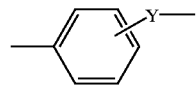

then Y cannot be 0; and when Z is —CH=CH—, n is 1,2,3, or 4; and when Y=vinyl, n=0;

R is CO₂H, CO₂lower alkyl, CO₂alkali metal, CH₂OH, CONHSO₂R³, CONHR³ᵃ, or

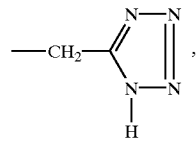

(—CH₂-5-tetrazolyl);

X is O, S or NH;

R¹ is hydrogen, lower alkyl, lower alkenyl, lower alkynyl, aralkyl, aryl, cycloalkyl, cycloalkylalkyl, cycloheteroalkyl, cycloheteroalkylalkyl, heteroaryl or heteroarylalkyl, or amide

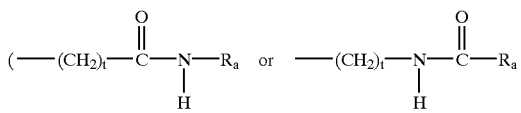

wherein t is 1 to 12 and $R_a$ is lower alkyl, aryl, cycloalkyl, or cycloalkylalkyl);

$R^2$ is hydrogen, lower alkyl, aryl, or aralkyl; or $R^1$ and $R^2$ together with the nitrogen to which they are linked may form a 5- to 8-membered ring;

$R^3$ is lower alkyl, aryl or aralkyl; and $R^{3a}$ is hydrogen, lower alkyl, aryl or aralkyl.

Ifetroban which is a particularly potent thromboxane $A_2$ antagonist is disclosed in the Misra et al patent and has the structure

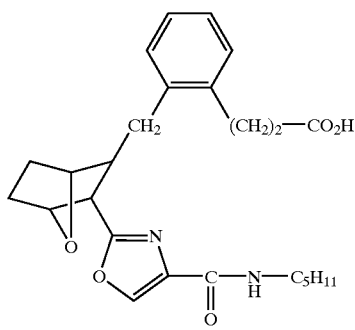

and the name [1S-(1α,2α,3α,4α)]-2-[[3-[4-[(pentylamino)carbonyl]-2-oxazolyl]-7-oxabicyclo[2.2.1]hept-2-yl]methyl]benzenepropanoic acid or a pharmaceutically acceptable salt thereof such as its sodium salt.

U.S. Pat. No. 5,312,818 to Rubin et al discloses use of thromboxane $A_2$ receptor antagonists in combination with anti-inflammatory agents including aspirin to prevent or treat ulcerative conditions caused by anti-inflammatory agents.

DESCRIPTION OF THE INVENTION

In accordance with the present invention, a method for preventing or inhibiting platelet aggregation and thrombus formation in mammals is provided wherein an ADP-receptor blocking antiplatelet drug, such as clopidogrel, in combination with a thromboxane $A_2$ receptor antagonist, such as ifetroban, and optionally a cholesterol lowering drug, is administered in therapeutically effective amounts to inhibit platelet aggregation and thrombus formation.

Furthermore, in accordance with the present invention, a method is provided for preventing or inhibiting onset of ischemic events including cardiovascular, cerebrovascular and peripheral vascular events, such as myocardial infarction, unstable and stable angina, acute reocclusion after percutaneous transluminal coronary angioplasty (PTCA), restenosis after PTCA, thrombotic stroke, transient ischemic attack, reversible ischemic neurological deficit, and intermittent claudication wherein a combination of an ADP-receptor blocking antiplatelet drug, such as clopidogrel, and a thromboxane $A_2$ receptor antagonist, such as ifetroban, and optionally a cholesterol lowering agent, is administered in therapeutic effective amounts.

In addition, in accordance with the present invention, a novel combination of antithrombotic agents is provided which includes an ADP receptor blocking antiplatelet drug, such as clopidogrel, and a thromboxane $A_2$ receptor antagonist, such as ifetroban, and optionally a cholesterol lowering drug, such as an HMG CoA reductase inhibitor such as pravastatin.

It is believed that the combination of ADP-receptor blocking antiplatelet drug and thromboxane $A_2$ receptor antagonist, which works by a mechanism other than inhibition of ADP-induced platelet aggregation, is a surprising and unique concept in treating diseases involved with platelet aggregation, thrombus formation and ischemic events, in that the combination may provide additional antiplatelet aggregation, anti-ischemic, anti-thrombus effects over that which may be obtained using each of the components of the combination alone. It may be expected that reduced levels of each of the ADP receptor blocking antiplatelet drug and thromboxane $A_2$ receptor antagonist may be employed to achieve desired results, albeit with reduced side effects.

In addition, in accordance with the present invention, a method is provided wherein a combination of an ADP-receptor blocking antiplatelet drug and a thromboxane $A_2$ receptor antagonist, and optionally aspirin, is employed to prevent or inhibit platelet aggregation and thrombus formation and to prevent or inhibit any of the disease states set out above, including thrombotic stroke.

The ADP-receptor blocking antiplatelet drug suitable for use herein includes antiplatelet drugs which inhibit ADP-induced platelet aggregation and include clopidogrel and/or ticlopidine and/or CS-747 (described herein), and do not include drugs such as aspirin which inhibit platelet aggregation by other mechanisms.

The term "clopidogrel" as employed herein includes clopidogrel in its free acid form, ester thereof, including the acetate, and/or pharmaceutically acceptable acid addition salts thereof, including the hydrogen sulfate salt.

The term "ticlopidine" as employed herein includes all pharmaceutical acceptable salts thereof including the hydrochloride salt thereof.

The term "CS-747" as employed herein includes 2-acetoxy-5-(α-cyclopropylcarbonyl-2-fluorobenzyl)-4,5,6,7-tetrahydrothieno[3,2-c]pyridine and pharmaceutically acceptable salts thereof.

Thromboxane $A_2$ receptor antagonists which may be employed herein include the interphenylene 7-oxabicycloheptyl substituted heterocyclic amide prostaglandin analogs as disclosed in U.S. Pat. No. 5,100,889, issued Mar. 31, 1992, including [1S-(1α,2α,3α,4α)]-2-[[3-[4-[[(4-cyclohexylbutyl)amino]carbonyl]-2-oxazolyl]-7-oxabicyclo[2.2.1]hept-2-yl]methyl]benzenepropanoic acid (SQ 33,961) which is preferred, or esters or salts thereof;

[1S-(1α,2α,3α,4α)]-2-[[3-[4-[[[(4-chlorophenyl)butyl]amino]carbonyl]-2-oxazolyl]-7-oxabicyclo[2.2.1]hept-2-yl]methyl]benzenepropanoic acid or esters, or salts thereof;

[1S-((1α,2α,3α,4α)]-3-[[3-[4-[[(4-cyclohexylbutyl)amino]carbonyl]-2-oxazolyl]-7-oxabicyclo[2.2.1]hept-2-yl]methyl]benzeneacetic acid, or esters or salts thereof;

[1S-((1α,2α,3α,4α)]-2-[[3-[4-[[(4-cyclohexylbutyl)amino]carbonyl]-2-oxazolyl]-7-oxabicyclo[2.2.1]hept-2-yl]methyl]phenoxy]acetic acid, or esters or salts thereof;

[1S-((1α,2α,3α,4α)]-2-[[3-[4-[[-7,7-dimethyloctyl)amino]carbonyl]-2-oxazolyl]-7-oxabicyclo[2.2.1]hept-2yl]methyl]benzenepropanoic acid, or esters or salts thereof and ifetroban, with ifetroban being most preferred;

7-oxabicycloheptyl substituted heterocyclic amide prostaglandin analogs as disclosed in U.S. Pat. No. 5,100,889, issued Mar. 31, 1992, including [1S-[1α,2α(Z),3α,4α)]-6-[3-[4-[[(4-cyclohexylbutyl)amino]carbonyl]-2-oxazolyl]-7-oxabicyclo[2.2.1]hept-2-yl]-4-hexenoic acid, or esters or salts thereof;

[1S-[1α,2α(Z),3α,4α)]]-6-[3-[4-[[(4-cyclohexylbutyl)amino]carbonyl]-2-thiazolyl]-7-oxabicyclo[2.2.1]hept-2-yl]-4-hexenoic acid, or esters or salts thereof;

[1S-[1α,2α(Z),3α,4α)]]-6-[3-[4-[[(4-cyclohexylbutyl)methylamino]carbonyl]-2-oxazolyl]-7-oxabicyclo[2.2.1]hept-2-yl]-4-hexenoic acid, or esters or salts thereof;

[1S-[1α,2α(Z),3α,4α)]]-6-[3-[4-[(1-pyrrolidinyl)carbonyl]-2-oxazolyl]-7-oxabicyclo[2.2.1]hept-2-yl]-4-hexenoic acid, or esters or salts thereof;

[1S-[1α,2α(Z),3α,4α)]]-6-[3-[4-[(cyclohexylamino)carbonyl]-2-oxazolyl]-7-oxabicyclo[2.2.1]hept-2-yl-4-hexenoic acid or esters or salts thereof;

[1S-[1α,2α(Z),3α,4α)]]-6-[3-[4-[[(2-cyclohexylethyl)amino]carbonyl]-2-oxazolyl]-7-oxabicyclo[2.2.1]hept-2-yl]-4-hexenoic acid, or esters or salts thereof;

[1S-[1α,2α(Z),3α,4α)]]-6-[3-[4-[[[2-(4-chloro-phenyl)ethyl]amino]carbonyl]-2-oxazolyl]-7-oxabicyclo-[2.2.1]hept-2-yl]-4-hexenoic acid, or esters or salts thereof;

[1S-[1α,2α(Z),3α,4α)]]-6-[3-[4-[[(4-chlorophenyl)amino]carbonyl]-2-oxazolyl]-7-oxabicyclo[2.2.1]hept-2-yl]-4-hexenoic acid, or esters or salts thereof;

[1S-[1α,2α(Z),3α,4α)]]-6-[3-[4-[[[4-(4-chlorophenyl)butyl]amino]carbonyl]-2-oxazolyl]-7-oxabicyclo[2.2.1]hept-2-yl]-4-hexenoic acid, or esters or salts thereof;

[1S-[1α,2α(Z),3α,4α)]]-6-[3-[4a-[[(6-cyclohexylhexyl)amino]carbonyl]-2-oxazolyl]-7-oxabicyclo[2.2.1]hept-2-yl]-4-hexenoic acid, or esters, or salts thereof;

[1S-[1α,2α(Z),3α,4α)]]-6-[3-[4-[[(6-cyclohexylhexyl)amino]carbonyl]-2-oxazolyl]-7-oxabicyclo[2.2.1]hept-2-yl]-4-hexenoic acid, or esters or salts thereof;

[1S-[1α,2α(Z),3α,4α)]]-6-[3-[4-[(propylamino)carbonyl]-2-oxazolyl]-7-oxabicyclo[2.2.1]hept-2-yl]-4-hexenoic acid, or esters or salts thereof;

[1S-[1α,2α(Z),3α,4α)]]-6-[3-[4-[[(4-butylphenyl)amino]carbonyl]-2-oxazolyl]-7-oxabicyclo[2.2.1]hept-2-yl]-4-hexenoic acid, or esters or salts thereof;

[1S-[1α,2α(Z),3α,4α)]]-6-[3-[4-[(2,3-dihydro-1H-indol-1-yl)carbonyl]-2-oxazolyl]-7-oxabicyclo[2.2.1]hept-2-yl]-4-hexenoic acid, or esters or salts thereof;

[1S-[1α,2α(Z),3α,4α)]]-6-[3-[4-[[(4-cyclohexylbutyl)amino]carbonyl]-2-oxazolyl]-7-oxabicyclo[2.2.1]hept-2-yl]-N-(phenylsulfonyl)-4-hexenamide;

[1S-[1α,2α(Z),3α,4α)]]-6-[3-[4-[[(4-cyclohexylbutyl)amino]carbonyl]-2-oxazolyl]-N-(methylsulfonyl)-7-oxabicyclo[2.2.1]hept-2-yl]-4-hexenamide;

[1S-[1α,2α(Z),3α,4α)]]-7-[3-[4-[[(4-cyclohexylbutyl)amino]carbonyl]-2-oxazolyl]-7-oxabicyclo[2.2.1]hept-2-yl]-5-heptenoic acid, or esters or salts thereof;

[1S-[1α,2α(Z),3α,4α)]]-6-[3-[4-[[(4-cyclohexylbutyl)amino]carbonyl]-1H-imidazol-2-yl]-7-oxabicyclo-[2.2.1]hept-2-yl]-4-hexenoic acid or esters or salts thereof;

[1S-[1α,2α,3α,4α)]-6-[3-[4-[[(7,7-dimethyloctyl)amino]carbonyl]-2-oxazolyl]-7-oxabicyclo[2.2.1]hept-2-yl]-4-hexenoic acid, or esters or salts thereof;

[1S-[1α,2α(E),3α,4α)]]-6-[3-[4-[[(4-cyclohexylbutyl)amino]carbonyl]-2-oxazolyl]-7-oxabicyclo[2.2.1]hept-2-yl]-4-hexenoic acid;

[1S-[1α,2α,3α,4α)]]-3-[4-[[(4-(cyclohexylbutyl)amino]carbonyl]-2-oxazolyl]-7-oxabicyclo[2.2.1]heptane-2-hexanoic acid or esters or salts thereof, with a preferred compound being [1S-[1α,2α(Z),3α,4α)]]-6-[3-[4-[[(4-cyclohexylbutyl)amino]carbonyl]-2-oxazolyl]-7-oxabicyclo-[2.2.1]hept-2-yl]-4-hexenoic acid, or esters or salts thereof;

7-oxabicycloheptane and 7-oxabicycloheptene compounds disclosed in U.S. Pat. No. 4,537,981 to Snitman et al, especially [1S-[1α,2α(Z),3α(1E,3S*,4R*),4α)]]-7-[3-(3-hydroxy-4-phenyl-1-pentenyl)-7-oxabicyclo[2.2.1]hept-2-yl]-5-heptenoic acid (SQ 29,548); the 7-oxabicycloheptane substituted aminoprostaglandin analogs disclosed in U.S. Pat. No. 4,416,896 to Nakane et al, especially, [1S-[1α,2α(Z),3α,4α)]]-7-[3-[[2-(phenylamino)carbonyl]hydrazino]methyl]-7-oxabicyclo[2.2.1]hept-2-yl]-5-heptenoic acid; the 7-oxabicycloheptane substituted diamide prostaglandin analogs disclosed in U.S. Pat. No. 4,663,336 to Nakane et al, especially, [1S-[1α,2α(Z),3α,4α)]]-7-[3-[[[[(1-oxoheptyl)amino]acetyl]amino]methyl]-7-oxabicyclo[2.2.1]hept-2-yl]-5-heptenoic acid and the corresponding tetrazole, and [1S-[1α,2α(Z),3α,4α)]]-7-[3-[[[[(4-cyclohexyl-1-oxobutyl)amino]acetyl]amino]methyl]-7-oxabicyclo]2.2.1]hept-2-yl]-5-heptenoic acid;

7-oxabicycloheptane imidazole prostaglandin analogs as disclosed in U.S. Pat. No. 4,977,174, issued Dec. 11, 1990, including [1S-[1α,2α(Z),3α,4α)]]-6-[3-[[4-(4-cyclohexyl-1-hydroxybutyl)-1H-imidazole-1-yl]methyl]-7-oxabicyclo[2.2.1]hept-2-yl]-4-hexenoic acid or its methyl ester;

[1S-[1α,2α(Z),3α,4α)]]-6-[3-[[4-(3-cyclohexylpropyl)-1H-imidazol-1-yl]methyl]-7-oxabicyclo[2.2.1]hept-2-yl]-4-hexenoic acid or its methyl ester;

[1S-[1α,2α(Z),3α,4α)]]-6-[3-[[4-(4-cyclohexyl-1-oxobutyl)-1H-imidazol-1-yl]methyl]-7-oxabicyclo[2.2.1]hept-2-yl]-4-hexenoic acid or its methyl ester;

[1S-[1α,2α(Z),3α,4α)]]-6-[3-(1H-imidazol-1-ylmethyl)-7-oxabicyclo[2.2.1]hept-2-yl]-4-hexenoic acid or its methyl ester; or

[1S-[1α,2α(Z),3α,4α)]]-6-[3-[[4-[[(4-cyclohexylbutyl)amino]carbonyl]-1H-imidazol-1-yl]methyl-7-oxabicyclo-[2.2.1]hept-2-yl]-4-hexenoic acid, or its methyl ester;

the phenoxyalkyl carboxylic acids disclosed in U.S. Pat. No. 4,258,058 to Witte et al, especially 4-[2-(benzenesulfamido)ethyl]phenoxyacetic acid (BM 13, 177—Boehringer Mannheim), the sulphonamidophenyl carboxylic acids disclosed in U.S. Pat. No. 4,443,477 to Witte et al, especially 4-[2-(4-chlorobenzenesulfonamido)ethyl]phenylacetic acid (BM 13,505, Boehringer Mannheim), the arylthioalkylphenyl carboxylic acids disclosed in U.S. Pat. No. 4,752,616, especially 4-(3-((4-chlorophenyl)sulfonyl)propyl)benzeneacetic acid.

Other examples of thromboxane $A_2$ receptor antagonists suitable for use herein include, but are not limited to yapiprost (which is a preferred example), (E)-5-[[[(pyridinyl)[3-(trifluoromethyl)phenyl]methylene]amino]oxy]pentanoic acid also referred to as R68,070—Janssen Research Laboratories, 3-[1-(4-chlorophenylmethyl)-5-fluoro-3-methylindol-2-yl]-2,2-dimethylpropanoic acid [(L-655240 Merck-Frosst) Eur. J. Pharmacol. 135(2):193, Mar.

17, 1987], 5(Z)-7-([2,4,5-cis]-4-(2-hydroxyphenyl)-2-trifluoromethyl-1,3-dioxan-5-yl)heptenoic acid (ICI 185282, Brit. J. Pharmacol. 90 (Proc. Suppl):228 P-Abs, March 87), 5(Z)-7-[2,2-dimethyl-4-phenyl-1,3-dioxan-cis-5-yl]heptenoic acid (ICI 159995, Brit. J. Pharmacol. 86 (Proc. Suppl):808 P-Abs., December 85), N,N'-bis[7-(3-chlorobenzeneaminosulfonyl)-1,2,3,4-tetrahydro-isoquinolyl]disulfonylimide (SKF 88046, Pharmacologist 25(3):116 Abs., 117 Abs, August 83), [1α(Z)-2β,5α]-(+)-7-[5-[[(1,1'-biphenyl)-4-yl]methoxy]-2-(4-morpholinyl)-3-oxocyclopentyl]-4-heptenoic acid (AH 23848—Glaxo, Circulation 72(6):1208, December 85, levallorphan allyl bromide (CM 32,191 Sanofi, Life Sci. 31 (20–21):2261, Nov. 15, 1982), (Z,2-endo-3-oxo)-7-(3-acetyl-2-bicyclo[2.2.1]heptyl-5-hepta-3Z-enoic acid, 4-phenyl-thiosemicarbazone (EP092—Univ. Edinburgh, Brit. J. Pharmacol. 84(3):595, March 85); GR 32,191 (Vapiprost)—[1R-[1α(Z), 2β,3β,5α]]-(+)-7-[5-([1,1'-biphenyl]-4-ylmethoxy)-3-hydroxy-2-(1-piperidinyl)cyclopentyl]-4-heptenoic acid; ICI 192,605—4(Z)-6-[(2,4,5-cis)2-(2-chlorophenyl)-4-(2-hydroxyphenyl)-1,3-dioxan-5-yl]hexenoic acid; BAY u 3405 (ramatroban)—3-[[(4-fluorophenyl)sulfonyl]amino]-1,2,3,4-tetrahydro-9H-carbazole-9-propanoic acid; or ONO 3708—7-[2α,4α-(-(di-methylmethano)-6β-(2-cyclopentyl-2β-hydroxyacetamido)-1α-cyclohexyl]-5(Z)-heptenoic acid; (±)(5Z)-7-[3-endo-[(phenylsulfonyl)amino]bicyclo[2.2.1]hept-2-exo-yl]-heptenoic acid (S-1452, Shionogi domitroban, Anboxan®); (−)6,8-difluoro-9-p-methylsulfonylbenzyl-1,2,3,4-tetrahydrocarbazol-1-yl-acetic acid (L670596, Merck) and (3-[1-(4-chlorobenzyl)-5-fluoro-3-methyl-indol-2-yl]-2,2-dimethylpropanoic acid (L655240, Merck).

The disclosure of the above-mentioned U.S. patents are incorporated herein by reference.

The optional cholesterol lowering drug employed herein includes, but is not limited to, HMG CoA reductase inhibitors, MTP inhibitors, squalene synthetase inhibitors, fibrates, resins and the like.

The term "MTP" as employed herein refers to a polypeptide or protein complex that (1) if obtained from an organism (e.g., cows, humans, etc.), can be isolated from the microsomal fraction of homogenized tissue; and (2) stimulates the transport of triglycerides, cholesterol esters, or phospholipids from synthetic phospholipid vesicles, membranes or lipoproteins to synthetic vesicles, membranes, or lipoproteins and which is distinct from the cholesterol ester transfer protein [Drayna et al., *Nature* 327, 632–634 (1987)] which may have similar catalytic properties.

The combination of the invention will include the ADP-receptor blocking antiplatelet drug and thromboxane A₂ receptor antagonist in a weight ratio to each other within the range from about 1000:1 to about 0.001:1, preferably from about 0.05:1 to about 100:1.

When employed, the cholesterol lowering drug will be employed in a weight ratio to the ADP-receptor blocking antiplatelet drug of within the range of from about 1000:1 to about 0.001:1 and preferably from about 0.05:1 to about 100:1.

When present, the cholesterol lowering drug to be used in combination with the ADP-receptor blocking antiplatelet drug and thromboxane A₂ receptor antagonist in accordance with the present invention is preferably an HMG CoA reductase inhibitor.

The HMG CoA reductase inhibitors suitable for use herein include, but are not limited to, mevastatin and related compounds as disclosed in U.S. Pat. No. 3,983,140, lovastatin (mevinolin) and related compounds as disclosed in U.S. Pat. No. 4,231,938, pravastatin and related compounds such as disclosed in U.S. Pat. No. 4,346,227, simvastatin and related compounds as disclosed in U.S. Pat. Nos. 4,448,784 and 4,450,171, with pravastatin, lovastatin or simvastatin being preferred. Other HMG CoA reductase inhibitors which may be employed herein include, but are not limited to, fluvastatin, cerivastatin, atorvastatin, pyrazole analogs of mevalonolactone derivatives as disclosed in U.S. Pat. No. 4,613,610, indene analogs of mevalonolactone derivatives as disclosed in PCT application WO 86/03488, 6-[2-(substituted-pyrrol-1-yl)alkyl]pyran-2-ones and derivatives thereof as disclosed in U.S. Pat. No. 4,647,576, Searle's SC-45355 (a 3-substituted pentanedioic acid derivative) dichloroacetate, imidazole analogs of mevalonolactone as disclosed in PCT application WO 86/07054, 3-carboxy-2-hydroxy-propane-phosphonic acid derivatives as disclosed in French Patent No. 2,596,393, 2,3-di-substituted pyrrole, furan and thiophene derivatives as disclosed in European Patent Application No. 0221025, naphthyl analogs of mevalonolactone as disclosed in U.S. Pat. No. 4,686,237, octahydro-naphthalenes such as disclosed in U.S. Pat. No. 4,499,289, keto analogs of mevinolin (lovastatin) as disclosed in European Patent Application No. 0,142,146 A2, as well as other known HMG CoA reductase inhibitors.

In addition, phosphinic acid compounds useful in inhibiting HMG CoA reductase suitable for use herein are disclosed in GB 2205837.

MTP inhibitors to be employed in the methods of the invention include MTP inhibitors disclosed in Canadian Patent Application No. 2,091,102 (corresponding to U.S. application Ser. No. 117,362), U.S. application Ser. No. 472,067, filed Jun. 6, 1995, U.S. application Ser. No. 548, 811, U.S. application Ser. No. 08/767,923, filed Dec. 17, 1996, U.S. provisional application No. 60/017,253, and U.S. provisional application No. 60/017,254.

All of the above U.S. applications are incorporated herein by reference.

The MTP inhibitors disclosed in U.S. application Ser. No. 472,067, filed Jun. 6, 1995 are piperidine compounds of the structure

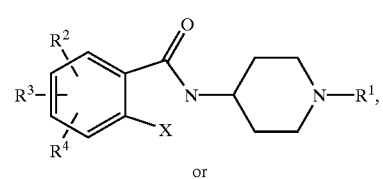

I or

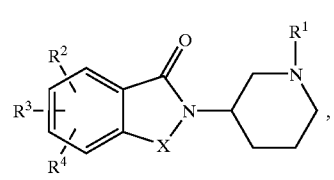

II or

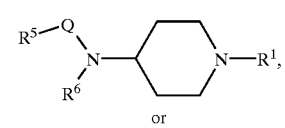

III or

-continued

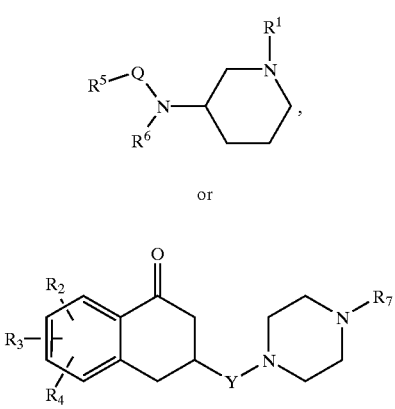

IV

V where Q is $-\overset{O}{\underset{\|}{C}}-$ or $-\overset{O}{\underset{\underset{\|}{O}}{\overset{\|}{S}}}-$ ;

X is: CHR$^8$, $-\overset{}{\underset{\underset{O}{\|}}{C}}-$ , $-\overset{}{\underset{R^9}{C}}H-\overset{}{\underset{R^{10}}{C}}H-$ or $-\overset{}{\underset{R^9}{C}}=\overset{}{\underset{R^{10}}{C}}-$ ;

R$^8$, R$^9$ and R$^{10}$ are independently hydrogen, alkyl, alkenyl, alkynyl, aryl, arylalkyl, heteroaryl, heteroarylalkyl, cycloalkyl, or cycloalkylalkyl;

Y is $-(CH_2)\overline{_m}-$ or $-\overset{}{\underset{\underset{O}{\|}}{C}}-$ wherein m is 2 or 3;

R$^1$ is alkyl, alkenyl, alkynyl, aryl, heteroaryl, arylalkyl wherein alkyl has at least 2 carbons, diarylalkyl, arylalkenyl, diarylalkenyl, arylalkynyl, diarylalkynyl, diarylalkylaryl, heteroarylalkyl wherein alkyl has at least 2 carbons, cycloalkyl, or cycloalkylalkyl wherein alkyl has at least 2 carbons, all optionally substituted through available carbon atoms with 1, 2, 3 or 4 groups selected from halo, haloalkyl, alkyl, alkenyl, alkoxy, aryloxy, aryl, arylalkyl, alkylmercapto, arylmercapto, cycloalkyl, cycloalkylalkyl, heteroaryl, fluorenyl, heteroarylalkyl, hydroxy or oxo;

or R$^1$ is a fluorenyl-type group of the structure

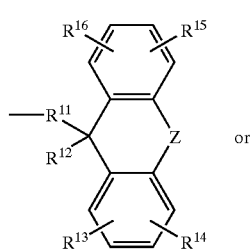

A

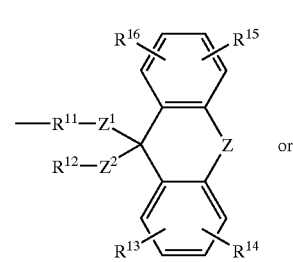

B

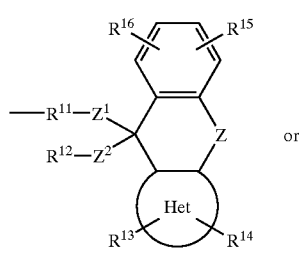

C

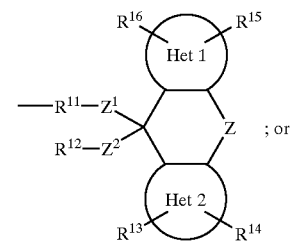

D

R$^1$ is an indenyl-type group of the structure

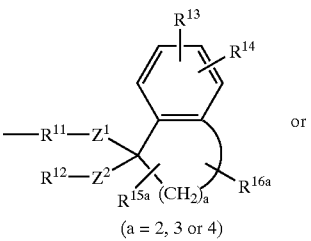

E (a = 2, 3 or 4)

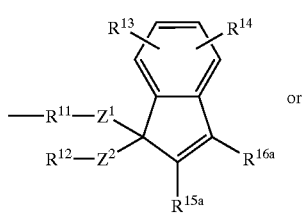

F

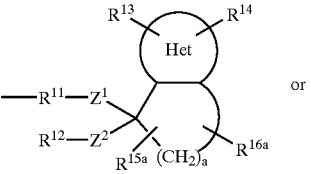

G

-continued

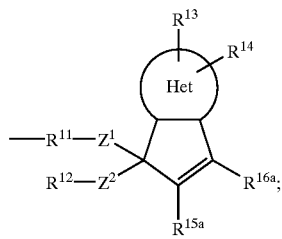

$Z^1$ and $Z^2$ are the same or different and are independently a bond, O, S,

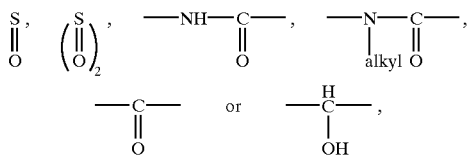

with the proviso that with respect to B, at least one of $Z^1$ and $Z^2$ will be other than a bond; $R^{11}$ is a bond, alkylene, alkenylene or alkynylene of up to 10 carbon atoms; arylene or mixed arylenealkylene; $R^{12}$ is hydrogen, alkyl, alkenyl, aryl, haloalkyl, trihaloalkyl, trihaloalkylalkyl, heteroaryl, heteroarylalkyl, arylalkyl, arylalkenyl, cycloalkyl, aryloxy, alkoxy, arylalkoxy or cycloalkylalkyl, with the provisos that
(1) when $R^{12}$ is H, aryloxy, alkoxy or arylalkoxy, then $Z^2$ is

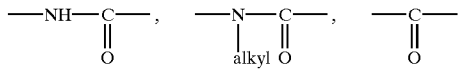

or a bond and
(2) when $Z^2$ is a bond, $R^{12}$ cannot be heteroaryl or heteroarylalkyl;

Z is bond, O, S, N-alkyl, N-aryl, or alkylene or alkenylene from 1 to 5 carbon atoms; $R^{13}$, $R^{14}$, $R^{15}$, and $R^{16}$ are independently hydrogen, alkyl, halo, haloalkyl, aryl, cycloalkyl, cycloheteroalkyl, alkenyl, alkynyl, hydroxy, alkoxy, nitro, amino, thio, alkylsulfonyl, arylsulfonyl, alkylthio, arylthio, aminocarbonyl, alkylcarbonyloxy, arylcarbonylamino, alkylcarbonylamino, arylalkyl, heteroaryl, heteroarylalkyl or aryloxy;

$R^{15a}$ and $R^{16a}$ are independently hydrogen, alkyl, halo, haloalkyl, aryl, cycloalkyl, cycloheteroalkyl, alkenyl, alkynyl, alkoxy, alkylsulfonyl, arylsulfonyl, alkylthio, arylthio, aminocarbonyl, alkylcarbonyloxy, arylcarbonylamino, alkylcarbonylamino, arylalkyl, heteroaryl, heteroarylalkyl, or aryloxy;

or $R^1$ is a group of the structure

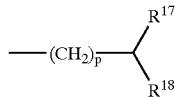

wherein
p is 1 to 8 and $R^{17}$ and $R^{18}$ are each independently H, alkyl, alkenyl, aryl, arylalkyl, heteroaryl, heteroarylalkyl, cycloalkyl or cycloalkylalkyl at least one of $R^{17}$ and $R^{18}$ being other than H;

or $R^1$ is a group of the structure

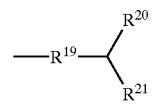

wherein
$R^{19}$ is aryl or heteroaryl;
$R^{20}$ is aryl or heteroaryl;
$R^{21}$ is H, alkyl, aryl, alkylaryl, arylalkyl, aryloxy, arylalkoxy, heteroaryl, heteroarylalkyl, heteroarylalkoxy, cycloalkyl, cycloalkylalkyl or cycloalkylalkoxy;
$R^2$, $R^3$, $R^4$ are independently hydrogen, halo, alkyl, alkenyl, alkoxy, aryloxy, aryl, arylalkyl, alkylmercapto, arylmercapto, cycloalkyl, cycloalkylalkyl, heteroaryl, heteroarylalkyl, hydroxy or haloalkyl;
$R^5$ is independently alkyl, alkenyl, alkynyl, aryl, alkoxy, aryloxy, arylalkoxy, heteroaryl, arylalkyl, heteroarylalkyl, cycloalkyl, cycloalkylalkyl, polycycloalkyl, polycycloalkylalkyl, cycloalkenyl, cycloheteroalkyl, heteroaryloxy, cycloalkenylalkyl, polycycloalkenyl, polycycloalkenylalkyl, heteroarylcarbonyl, amino, alkylamino, arylamino, heteroarylamino, cycloalkyloxy, cycloalkylamino, all optionally substituted through available carbon atoms with 1, 2, 3 or 4 groups selected from hydrogen, halo, alkyl, haloalkyl, alkoxy, haloalkoxy, alkenyl, alkynyl, cycloalkyl, cycloalkylalkyl, cycloheteroalkyl, cycloheteroalkylalkyl, aryl, heteroaryl, arylalkyl, arylcycloalkyl, arylalkenyl, arylalkynyl, aryloxy, aryloxyalkyl, arylalkoxy, arylazo, heteroaryloxo, heteroarylalkyl, heteroarylalkenyl, heteroaryloxy, hydroxy, nitro, cyano, amino, substituted amino, thiol, alkylthio, arylthio, heteroarylthio, arylthioalkyl, alkylcarbonyl, arylcarbonyl, arylaminocarbonyl, alkoxycarbonyl, aminocarbonyl, alkynylaminocarbonyl, alkylaminocarbonyl, alkenylaminocarbonyl, alkylcarbonyloxy, arylcarbonyloxy, alkylcarbonylamino, arylcarbonylamino, arylsulfinyl, arylsulfinylalkyl, arylsulfonyl, alkylsulfonyl, arylsulfonylamino, heteroarylcarbonylamino, heteroarylsulfinyl, heteroarylthio, heteroarylsulfonyl, alkylsulfinyl;
$R^6$ is hydrogen or $C_1$–$C_4$ alkyl or $C_1$–$C_4$ alkenyl; all optionally substituted with 1, 2, 3 or 4 groups which may independently be any of the substituents listed in the definition of $R^5$ set out above;
$R^7$ is alkyl, aryl or arylalkyl wherein alkyl by itself or as part of arylalkyl is optionally substituted with oxo

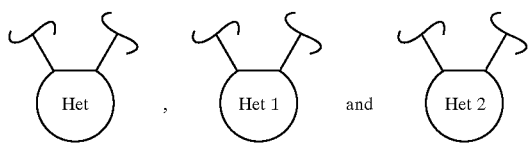

are the same or different and are independently selected from heteroaryl containing 5- or 6-ring members; and N-oxides

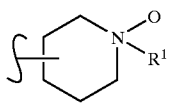

thereof; and pharmaceutically acceptable salts thereof.

The MTP inhibitors disclosed in U.S. application Ser. No. 548,811 filed Jan. 11, 1996, have the structure

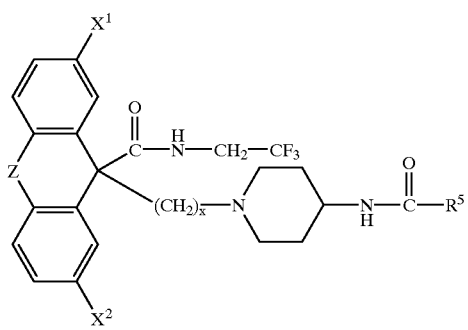

including the piperidine N-oxide thereof or a pharmaceutically acceptable salt thereof, wherein Z is a bond, O or S;

X$^1$ and X$^2$ are independently selected from H or halo;

x is an integer from 2 to 6;

R$^5$ is heteroaryl, aryl, heterocycloalkyl or cycloalkyl, each R$^5$ group being optionally substituted with 1, 2, 3 or 4 substituents which may be the same or different.

The MTP inhibitors disclosed in U.S. application Ser. No. 08/767,923, filed Dec. 17, 1996 have the structure

VII

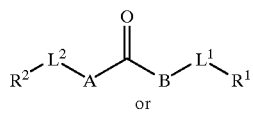

or

VIII

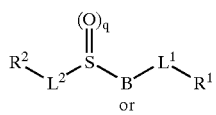

or

IX

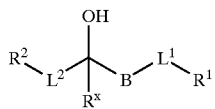

including pharmaceutically acceptable salts thereof, wherein q is 0, 1 or 2;

A is
(1) a bond;
(2) —O—; or (3) 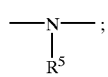

where R$^5$ is H or lower alkyl or R$^5$ together with R$^2$ forms a carbocyclic or heterocyclic ring system containing 4 to 8 members in the ring.

B is a fluorenyl-type group of the structure:

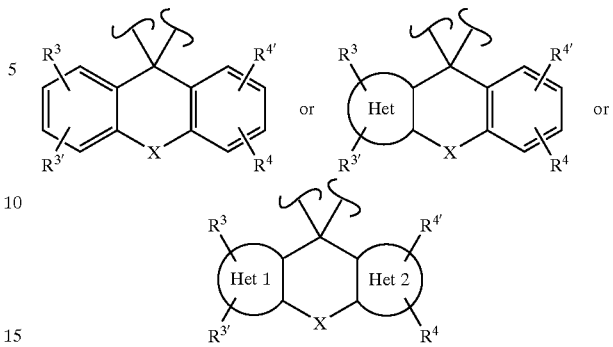

(the above B is also referred to as a fluorenyl-type ring or moiety); or

B is an indenyl-type group of the structure

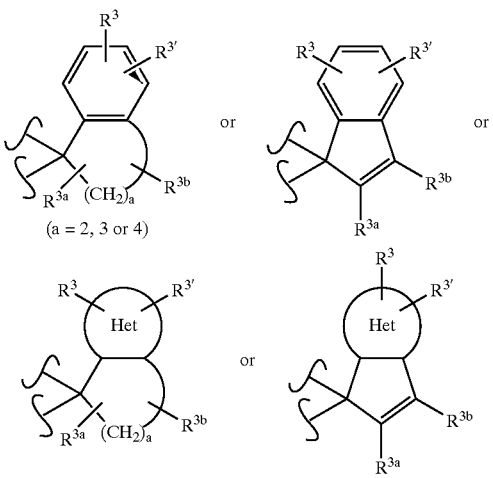

(the above B is also referred to as an indenyl-type ring or moiety);

R$^x$ is H, alkyl or aryl;

R$^1$ is alkyl, alkenyl, alkynyl, alkoxyl, (alkyl or aryl)$_3$Si (where each alkyl or aryl group is independent), cycloalkyl, cycloalkenyl, substituted alkylamino, substituted arylalkylamino, aryl, arylalkyl, arylamino, aryloxy, heteroaryl, heteroarylamino, heteroaryloxy, arylsulfonylamino, hetero-arylsulfonylamino, arylthio, arylsulfinyl, arylsulfonyl, alkylthio, alkylsulfinyl, alkylsulfonyl, heteroarylthio, heteroarylsulfinyl, heteroarylsulfonyl, —PO(R$^{13}$) (R$^{14}$), (where R$^{13}$ and R$^{14}$ are independently alkyl, aryl, alkoxy, aryloxy, heteroaryl, heteroarylalkyl, heteroaryloxy, heteroarylalkoxy, cycloheteroalkyl, cycloheteroalkylalkyl, cycloheteroalkoxy, or cycloheteroalkylalkoxy); R$^1$ can also be aminocarbonyl (where the amino may optionally be substituted with one or two aryl, alkyl or heteroaryl groups); cyano, 1,1-(alkoxyl or aryloxy)2alkyl (where the two aryl or alkyl substituents can be independently defined, or linked to one another to form a ring, such as 1,3-dioxane or 1,3-dioxolane, connected to L$^1$ (or L$^2$ in the case of R$^2$) at the 2-position); 1,3-dioxane or 1,3-dioxolane connected to L$^1$ (or L$^2$ in the case of R$^2$) at the 4-position.

The R$^1$ group may have from one to four substituents, which can be any of the R$^3$ groups or R$^1$ groups, and any of the preferred R$^1$ substituents set out below.

R[1] may be substituted with the following preferred substituents: alkylcarbonylamino, cycloalkylcarbonylamino, arylcarbonylamino, heteroarylcarbonylamino, alkoxycarbonylamino, aryloxycarbonylamino, heteroaryloxylcarbonylamino, uriedo (where the uriedo nitrogens may be substituted with alkyl, aryl or heteroaryl), heterocyclylcarbonylamino (where the heterocycle is connected to the carbonyl group via a nitrogen or carbon atom), alkylsulfonylamino, arylsulfonylamino, heteroarylsulfonylamino,

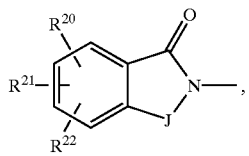

where
J is: CHR[23],

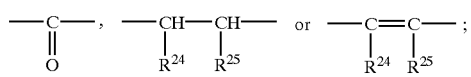

R[23], R[24] and R[25] are independently hydrogen, alkyl, alkenyl, alkynyl, aryl, arylalkyl, heteroaryl, heteroarylalkyl, cycloalkyl, or cycloalkylalkyl;

R[20], R[21] R[22] are independently hydrogen, halo, alkyl, alkenyl, alkoxy, aryloxy, aryl, arylalkyl, alkylmercapto, arylmercapto, cycloalkyl, cycloalkylalkyl, heteroaryl, heteroarylalkyl, hydroxy or haloalkyl; and these preferred substituents may either be directly attached to R[1], or attached via an alkylene chain at an open position.

R[2] is the same or different from R[1] and is independently any of the groups set out for R[1], H, polyhaloalkyl (such as $CF_3CH_2$, $CF_3CF_2CH_2$ or $CF_3$) or cycloheteroalkyl, and may be substituted with one to four of any of the groups defined for R[3], or any of the substituents preferred for R[1].

L[1] is a linking group containing from 1 to 10 carbons in a linear chain (including alkylene, alkenylene or alkynylene), which may contain, within the linking chain any of the following: one or two alkenes, one or two alkynes, an oxygen, an amino group optionally substituted with alkyl or aryl, an oxo group; and may be substituted with one to five alkyl or halo groups (preferably F).

L[2] may be the same or different from L[1] and may independently be any of the L[1] groups set out above or a singe bond.

R[3], R[3'], R[4] and R[4'] may be the same or different and are independently selected from H, halogen, $CF_3$, haloalkyl, hydroxy, alkoxy, alkyl, aryl, alkenyl, alkenyloxy, alkynyl, alkynyloxy, alkanoyl, nitro, amino, thiol, alkylthio, alkylsulfinyl, alkylsulfonyl, carboxy, alkoxycarbonyl, aminocarbonyl, alkylcarbonyloxy, alkylcarbonylamino, cycloheteroalkyl, cycloheteroalkylalkyl, cyano, Ar, Ar-alkyl, ArO, Ar-amino, Ar-thio, Ar-sulfinyl, Ar-sulfonyl, Ar-carbonyl, Ar-carbonyloxy or Ar-carbonylamino, wherein Ar is aryl or heteroaryl and Ar may optionally include 1, 2 or 3 additional rings fused to Ar;

R[3a] and R[3b] are the same or different and are independently any of the R[3] groups except hydroxy, nitro, amino or thio;

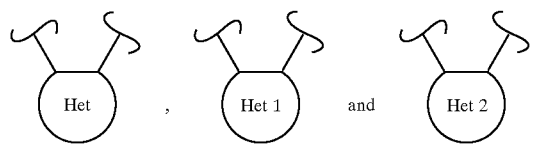

are the same or different and independently represent a 5 or 6 membered heteroaryl ring which may contain 1, 2, 3 or 4 heteroatoms in the ring which are independently N, S or O; and including N-oxides.

X (in the fluorenyl type ring) is a bond, or is one of the following groups:

 (1)

 (2)

 (3)

(4)

(5)

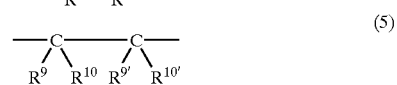

(6)

(7)

wherein

Y is O, N—R[6] or S;

n' is 0, 1 or 2;

R[6] is H, lower alkyl, aryl, —C(O)—R[11] or —C(O)—O—R[11];

R[7] and R[8] are the same or different and are independently H, alkyl, aryl, halogen, —O—R[12], or R[7] and R[8] together can be oxygen to form a ketone;

R[9], R[10], R[9'] and R[10'] are the same or different and are independently H, lower alkyl, aryl or —O—R[11];

R[9"] and R[10"] are the same or different and are independently H, lower alkyl, aryl, halogen or —O—R[11];

R[11] is alky or aryl;

R[12] is H, alkyl or aryl.

The various provisos for compounds set out in U.S. application Ser. No. 472,067, filed Jun. 6, 1995 and U.S. application Ser. No. 08/767,923, filed Dec. 17, 1996 are not applicable here.

The MTP inhibitors disclosed in U.S. provisional application No. 60/017,253, filed May 10, 1996, are pyrrolidine compounds and have the structure

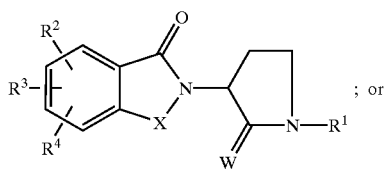
X

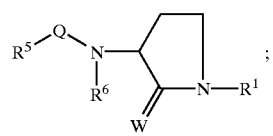
XI

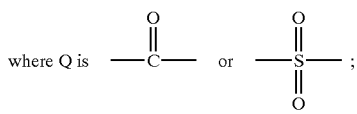

where Q is —C(=O)— or —S(=O)(=O)—;

W is H,H or O;

X is: CHR⁸, —C(=O)—, —CH(R⁹)—CH(R¹⁰)— or —C(R⁹)=C(R¹⁰)—;

$R^8$, $R^9$ and $R^{10}$ are independently hydrogen, alkyl, alkenyl, alkynyl, aryl, arylalkyl, heteroaryl, heteroarylalkyl, cycloalkyl, or cycloalkylalkyl;

$R^1$ is alkyl, alkenyl, alkynyl, aryl, heteroaryl, arylalkyl (wherein alkyl preferably has at least 2 carbons, more preferably at least 3 carbons), diarylalkyl, arylalkenyl, diarylalkenyl, arylalkynyl, diarylalkynyl, diarylalkylaryl, heteroarylalkyl (wherein alkyl preferably has at least 2 carbons, more preferably at least 3 carbons), cycloalkyl, or cycloalkylalkyl (wherein alkyl preferably has at least 2 carbons, more preferably at least 3 carbons); all of the aforementioned $R^1$ groups being optionally substituted through available carbon atoms with 1, 2, 3 or 4 groups selected from halo, haloalkyl, alkyl, alkenyl, alkoxy, aryloxy, aryl, arylalkyl, alkylmercapto, arylmercapto, cycloalkyl, cycloalkylalkyl, heteroaryl, fluorenyl, heteroarylalkyl, hydroxy or oxo; or $R^1$ is a fluorenyl-type group of the structure

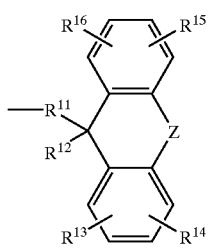
A

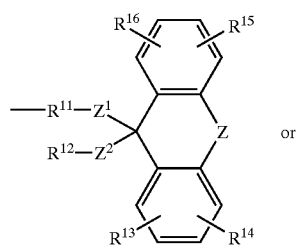
B

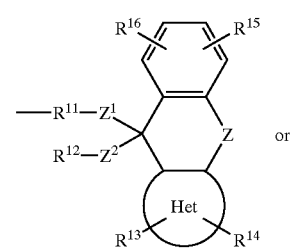
C

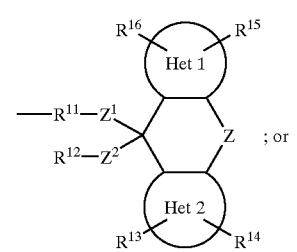
D $R^1$ is an indenyl-type group of the structure

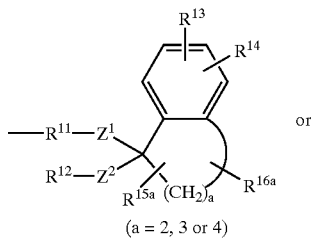
E (a = 2, 3 or 4)

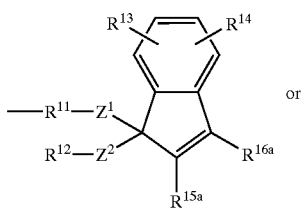
F

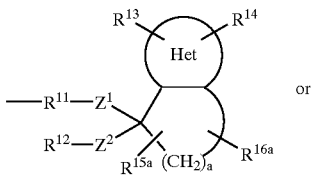
G

-continued

[Structure: cyclopentene fused with Het ring bearing R13, R14; with R11—Z1, R12—Z2, R15a, R16a substituents]

$Z^1$ and $Z^2$ are the same or different and are independently a bond, O, S, $\overset{S}{\underset{O}{\|}}$, $\left(\overset{S}{\underset{O}{\|}}\right)_2$, —NH—C(=O)—, —N(alkyl)—C(=O)—, —C(=O)— or —CH(OH)—, with the proviso that with respect to B, at least one of $Z^1$ and $Z^2$ will be other than a bond;

$R^{11}$ is a bond, alkylene, alkenylene or alkynylene of up to 10 carbon atoms, arylene (for example —[phenylene]—), or mixed arylene-alkylene (for example —[phenylene]—(CH$_2$)$_{\overline{n}}$—)

where
n is 1 to 6;
$R^{12}$ is hydrogen, alkyl, alkenyl, aryl, haloalkyl, trihaloalkyl, trihaloalkylalkyl, heteroaryl, heteroarylalkyl, arylalkyl, arylalkenyl, cycloalkyl, aryloxy, alkoxy, arylalkoxy or cycloalkylalkyl; with the provisos that (1) when $R^{12}$ is H, aryloxy, alkoxy or arylalkoxy, then $Z^2$ is —NH—C(=O)—, —N(alkyl)—C(=O)—, —C(=O)— or a bond;
and (2) when $Z^2$ is a bond, $R^{12}$ cannot be heteroaryl or heteroarylalkyl;
Z is a bond, O, S, N-alkyl, N-aryl, or alkylene or alkenylene of from 1 to 5 carbon atoms;
$R^{13}$, $R^{14}$, $R^{15}$, and $R^{16}$ are independently hydrogen, alkyl, halo, haloalkyl, aryl, cycloalkyl, cycloheteroalkyl, alkenyl, alkynyl, hydroxy, alkoxy, nitro, amino, thio, alkylsulfonyl, arylsulfonyl, alkylthio, arylthio, aminocarbonyl, alkylcarbonyloxy, arylcarbonylamino, alkylcarbonylamino, arylalkyl, heteroaryl, heteroarylalkyl, or aryloxy;
$R^{15a}$ and $R^{16a}$ are independently any of the $R^{15}$ or $R^{16}$ groups except hydroxy, nitro, amino or thio;

$R^1$

—(CH$_2$)$_p$—CH(R$^{17}$)(R$^{18}$)

wherein
p is 1 to 8 and $R^{17}$ and $R^{18}$ are each independently H, alkyl, alkenyl, aryl, arylalkyl, heteroaryl, heteroarylalkyl, cycloalkyl or cycloalkylalkyl, at least one of $R^{17}$ and $R^{18}$ being other than H;
or $R^1$ is

—R$^{19}$—C(R$^{20}$)(R$^{21}$)

wherein
$R^{19}$ is aryl or heteroaryl;
$R^{20}$ is aryl or heteroaryl;
$R^{21}$ is H, alkyl, aryl, alkylaryl, arylalkyl, aryloxy, arylalkoxy, heteroaryl, heteroarylalkyl, heteroarylalkoxy, cycloalkyl, cycloalkylalkyl or cycloalkylalkoxy;
$R^2$, $R^3$, $R^4$ are independently hydrogen, halo, alkyl, alkenyl, alkoxy, aryloxy, aryl, arylalkyl, alkylmercapto, arylmercapto, cycloalkyl, cycloalkylalkyl, heteroaryl, heteroarylalkyl, hydroxy or haloalkyl;
$R^5$ is alkyl, alkenyl, alkynyl, aryl, alkoxy, aryloxy, arylalkoxy, heteroaryl, arylalkyl, heteroarylalkyl, cycloalkyl, cycloheteroalkyl, heteroaryloxy, cycloalkylalkyl, polycycloalkyl, polycycloalkylalkyl, cycloalkenyl, cycloalkenylalkyl, polycycloalkenyl, polycycloalkenylalkyl, heteroarylcarbonyl, amino, alkylamino, arylamino, heteroarylamino, cycloalkyloxy, cycloalkylamino, all of the $R^5$ substituents and $R^6$ substituents (set out hereinafter) being optionally substituted through available carbon atoms with 1, 2, 3 or 4 groups selected from hydrogen, halo, alkyl, haloalkyl, alkoxy, haloalkoxy, alkenyl, alkynyl, cycloalkyl, cycloalkylalkyl, cycloheteroalkyl, cycloheteroalkylalkyl, aryl, heteroaryl, arylalkyl, arylcycloalkyl, arylalkenyl, arylalkynyl, aryloxy, aryloxyalkyl, arylalkoxy, arylazo, heteroaryloxo, heteroarylalkyl, heteroarylalkenyl, heteroaryloxy, hydroxy, nitro, cyano, amino, substituted amino (wherein the amino includes 1 or 2 substituents which are alkyl, aryl or heteroaryl, or any of the other aryl compounds mentioned in the definitions), thiol, alkylthio, arylthio, heteroarylthio, arylthioalkyl, alkylcarbonyl, arylcarbonyl, arylaminocarbonyl, alkoxycarbonyl, aminocarbonyl, alkynylaminocarbonyl, alkylaminocarbonyl, alkenylaminocarbonyl, alkylcarbonyloxy, arylcarbonyloxy, alkylcarbonylamino, arylcarbonylamino, arylsulfinyl, arylsulfinylalkyl, arylsulfonyl, alkylsulfonyl, arylsulfonylamino, heteroarylcarbonylamino, heteroarylsulfinyl, heteroarylthio, heteroarylsulfonyl, or alkylsulfinyl. Where $R^5$ is phenyl, aryl, heteroaryl or cycloalkyl; this group preferably includes an ortho hydrophobic substituent such as alkyl, haloalkyl (with up to 5 halo groups), alkoxy, haloalkoxy (with up to 5 halo groups), aryl, aryloxy or arylalkyl;

$R^6$ is hydrogen or $C_1$–$C_4$ alkyl or $C_1$–$C_4$ alkenyl;

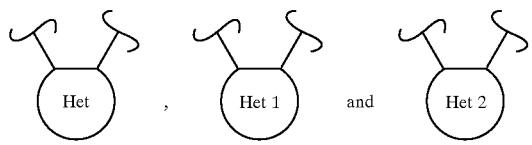

are the same or different and are independently selected from heteroaryl containing 5- or 6-ring members; and
including N-oxides of the formulae I and II compounds, that is

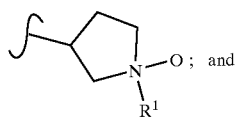; and including pharmaceutically acceptable salts thereof.

The MTP inhibitors disclosed in U.S. provisional application No. 60/017,254, filed May 10, 1996, are azetidine compounds which have the structure

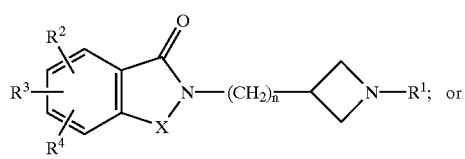    XII

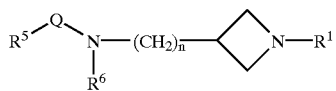    XIII

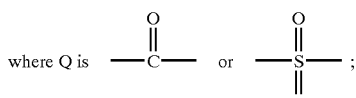

n is 0 or 1; $R^8$, $R^9$ and $R^{10}$ are independently hydrogen, alkyl, alkenyl, alkynyl, aryl, arylalkyl, heteroaryl, heteroarylalkyl, cycloalkyl, or cycloalkylalkyl;

$R^1$ is alkyl, alkenyl, alkynyl, aryl, heteroaryl, arylalkyl (wherein alkyl preferably has at least 2 carbons, more preferably at least 3 carbons), diarylalkyl, arylalkenyl, diarylalkenyl, arylalkynyl, diarylalkynyl, diarylalkylaryl, heteroarylalkyl (wherein alkyl preferably has at least 2 carbons, more preferably at least 3 carbons), cycloalkyl, or cycloalkylalkyl (wherein alkyl preferably has at least 2 carbons, more preferably at least 3 carbons); all of the aforementioned $R^1$ groups being optionally substituted through available carbon atoms with 1, 2, 3 or 4 groups selected from halo, haloalkyl, alkyl, alkenyl, alkoxy, aryloxy, aryl, arylalkyl, alkylmercapto, arylmercapto, cycloalkyl, cycloalkylalkyl, heteroaryl, fluorenyl, heteroarylalkyl, hydroxy or oxo; or $R^1$ is a fluorenyl-type group of the structure

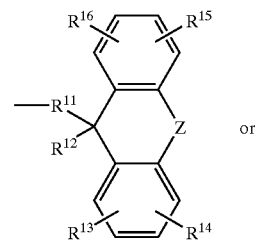    A

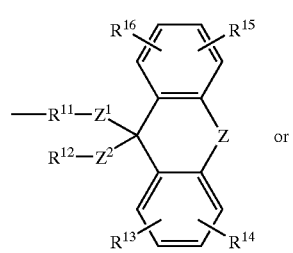    B

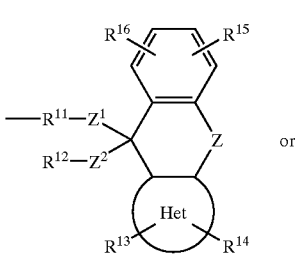    C

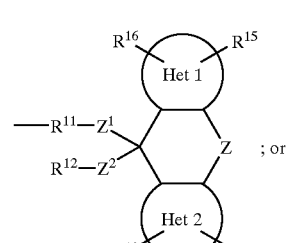    D $R^1$ is an indenyl-type group of the structure

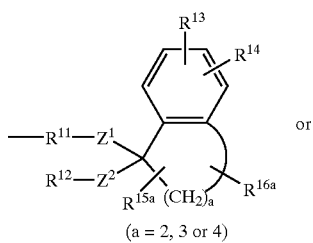    E

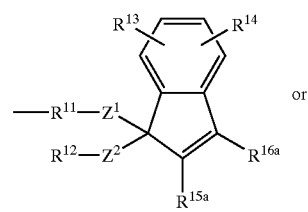    F

-continued

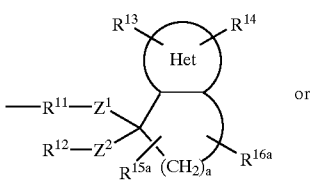

G

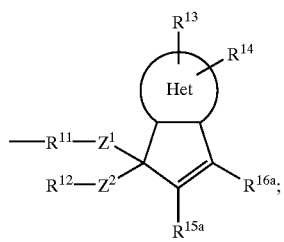

H $Z^1$ and $Z^2$ are the same or different and are independently a bond, O, S,

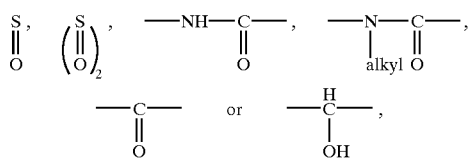

with the proviso that with respect to B, at least one of $Z^1$ and $Z^2$ will be other than a bond;

$R^{11}$ is a bond, alkylene, alkenylene or alkynylene of up to 10 carbon atoms, arylene (for example

), or mixed arylene-alkylene (for example

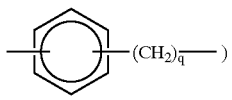)

where q is 1 to 6;

$R^{12}$ is hydrogen, alkyl, alkenyl, aryl, haloalkyl, trihaloalkyl, trihaloalkylalkyl, heteroaryl, heteroarylalkyl, arylalkyl, arylalkenyl, cycloalkyl, aryloxy, alkoxy, arylalkoxy or cycloalkylalkyl; with the provisos that (1) when $R^{12}$ is H, aryloxy, alkoxy or arylalkoxy, then $Z^2$ is

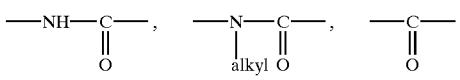

or a bond;

and (2) when $Z^2$ is a bond, $R^{12}$ cannot be heteroaryl or heteroarylalkyl;

Z is a bond, O, S, N-alkyl, N-aryl, or alkylene or alkenylene of from 1 to 5 carbon atoms;

$R^{13}$, $R^{14}$, $R^{15}$, and $R^{16}$ are independently hydrogen, alkyl, halo, haloalkyl, aryl, cycloalkyl, cycloheteroalkyl, alkenyl, alkynyl, hydroxy, alkoxy, nitro, amino, thio, alkylsulfonyl, arylsulfonyl, alkylthio, arylthio, aminocarbonyl, alkylcarbonyloxy, arylcarbonylamino, alkylcarbonylamino, arylalkyl, heteroaryl, heteroarylalkyl, or aryloxy;

$R^{15a}$ and $R^{16a}$ are independently any of the $R^{15}$ or $R^{16}$ groups except hydroxy, nitro, amino or thio;

or $R^1$ is

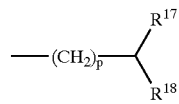

wherein p is 1 to 8 and $R^{17}$ and $R^{18}$ are each independently H, alkyl, alkenyl, aryl, arylalkyl, heteroaryl, heteroarylalkyl, cycloalkyl or cycloalkylalkyl, at least one of $R^{17}$ and $R^{18}$ being other than H;

or $R^1$ is

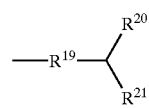

wherein $R^{19}$ is aryl or heteroaryl;

$R^{20}$ is aryl or heteroaryl;

$R^{21}$ is H, alkyl, aryl, alkylaryl, arylalkyl, aryloxy, arylalkoxy, heteroaryl, heteroarylalkyl, heteroarylalkoxy, cycloalkyl, cycloalkylalkyl or cycloalkylalkoxy;

$R^2$, $R^3$, $R^4$ are independently hydrogen, halo, alkyl, alkenyl, alkoxy, aryloxy, aryl, arylalkyl, alkylmercapto, arylmercapto, cycloalkyl, cycloalkylalkyl, heteroaryl, heteroarylalkyl, hydroxy or haloalkyl;

$R^5$ is alkyl, alkenyl, alkynyl, aryl, alkoxy, aryloxy, arylalkoxy, heteroaryl, arylalkyl, heteroarylalkyl, cycloalkyl, cycloheteroalkyl, heteroaryloxy, cycloalkylalkyl, polycycloalkyl, polycycloalkylalkyl, cycloalkenyl, cycloalkenylalkyl, polycycloalkenyl, polycycloalkenylalkyl, heteroarylcarbonyl, amino, alkylamino, arylamino, heteroarylamino, cycloalkyloxy, cycloalkylamino, all of the $R^5$ substituents and $R^6$ substituents (set out hereinafter) being optionally substituted through available carbon atoms with 1, 2, 3 or 4 groups selected from hydrogen, halo, alkyl, haloalkyl, alkoxy, haloalkoxy, alkenyl, alkynyl, cycloalkyl, cycloalkylalkyl, cycloheteroalkyl, cycloheteroalkylalkyl, aryl, heteroaryl, arylalkyl, arylcycloalkyl, arylalkenyl, arylalkynyl, aryloxy, aryloxyalkyl, arylalkoxy, arylazo, heteroaryloxo, heteroarylalkyl, heteroarylalkenyl, heteroaryloxy, hydroxy, nitro, cyano, amino, substituted amino (wherein the amino includes 1 or 2 substituents which are alkyl, aryl or heteroaryl, or any of the other aryl compounds mentioned in the definitions), thiol, alkylthio, arylthio, heteroarylthio, arylthioalkyl, alkylcarbonyl, arylcarbonyl, arylaminocarbonyl, alkoxycarbonyl, aminocarbonyl, alkynylaminocarbonyl, alkylaminocarbonyl, alkenylaminocarbonyl, alkylcarbonyloxy, arylcarbonyloxy, alkylcarbonylamino, arylcarbonylamino, arylsulfinyl, arylsulfinylalkyl, arylsulfonyl, alkylsulfonyl, arylsulfonylamino, heteroarylcarbonylamino, heteroarylsulfinyl, heteroarylthio, heteroarylsulfonyl, or alkylsulfinyl. Where $R^5$ is phenyl, aryl, heteroaryl or cycloalkyl; this group preferably includes an ortho hydrophobic substituent such as alkyl, haloalkyl (with up to 5 halo groups), alkoxy, haloalkoxy (with up to 5 halo groups), aryl, aryloxy or arylalkyl;

$R^6$ is hydrogen or $C_1$–$C_4$ alkyl or $C_1$–$C_4$ alkenyl;

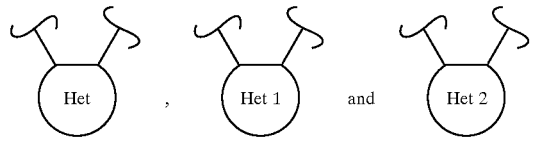

are the same or different and are independently selected from heteroaryl containing 5- or 6-ring members; and including N-oxides of the formulae I and II compounds, that is

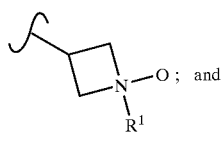

including pharmaceutically acceptable salts thereof.

Compounds disclosed as preferred in each of the above applications are preferred for use in the present invention.

Most preferred MTP inhibitors to be employed in accordance with the present invention include preferred MTP inhibitors as set out in U.S. patent application Ser. No. 548,811, filed Jan. 11, 1996 and in U.S. application Ser. No. 08/767,923, filed Dec. 17, 1996.

Thus, preferred compounds in U.S. patent application Ser. No. 548,811 for use herein are compounds designated VI above where Z is a bond;

$X^1$ and $X^2$ are H;

$R^5$ is aryl such as phenyl substituted with

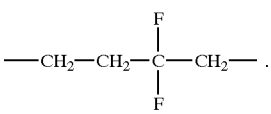

(1) aryl such as phenyl,
(2) heteroaryl such as

![benzothiazole and pyridine structures]

(3) halo such as Cl $R^5$ is heteroaryl such as

![thiophene structures] or substituted with
(1) aroyl such as

![benzoyl group]

(2) arylthio such as

![S-phenyl-Cl group]

wherein the $R^5$ substituent is preferably in the position adjacent to the carbon linked to $$\overset{O}{\underset{}{\overset{\|}{C}}}.$$

$(CH_2)_x$ is —$(CH_2)_4$— or $$—CH_2—CH_2—\overset{F}{\underset{F}{C}}—CH_2—.$$

Most preferred is 9-[4-[4-[[2-(2,2,2-Trifluoroethoxy)benzoyl]amino]-1-piperidinyl]butyl]-N-(2,2,2-trifluoroethyl)-9H-fluorene-9-carboxamide ![structure of the most preferred compound]

Preferred compounds in U.S. application Ser. No. 08/767,923 for use herein are MTP inhibitor compounds of formula I that is ![formula I structure: R²–L²–A–C(=O)–B–L¹–R¹]

wherein
A is NH,

B is

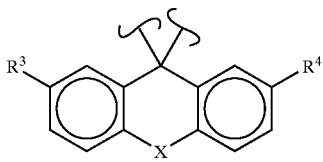

X is a bond, oxygen or sulfur; $R^3$ and $R^4$ are independently H or F.

Preferred $R^1$ groups are aryl, preferably phenyl, heteroaryl, preferably imidazoyl or pyridyl (preferably substituted with one of the preferred $R^1$ substituents: arylcarbonylamino, heteroarylcarbonylamino, cycloalkylcarbonylamino, alkoxycarbonylamino, alkylsulfonylamino, arylsulfonylamino, heteroarylsulfonylamino), $PO(OAlkyl)_2$, heteroarylthio, benzthi-azole-2-thio, imidazole-2-thio, alkyl, or alkenyl, cycloalkyl such as cyclohexyl, or 1,3-dioxan-2-yl.

Preferred $R^2$ groups are alkyl, polyfluoroalkyl (such as 1,1,1-trifluoroethyl), alkenyl, aryl or heteroaryl (preferably substituted with one of the preferred $R^1$ substituents above), or $PO(OAlkyl)_2$.

If $R^2$ is alkyl, 1,1,1-trifluoroethyl, or alkenyl, it is preferred that $R^1$ is other than alkyl or alkenyl.

It is preferred that $L^1$ contains 1 to 5 atoms in the linear chain and $L^2$ is a bond or lower alkylene.

Preferred embodiments of formula IA and formula IB compounds of the invention include those where B, $L^1$, $L^2$, $R^1$ and $R^2$ are as set out with respect to the preferred embodiments of the formula I compounds, q is 0 or 2 and $R^x$ is H.

Thus, preferred MTP inhibiting compounds for use herein and disclosed in U.S. application Ser. No. 08/767,923, filed Dec. 17, 1996, include the following

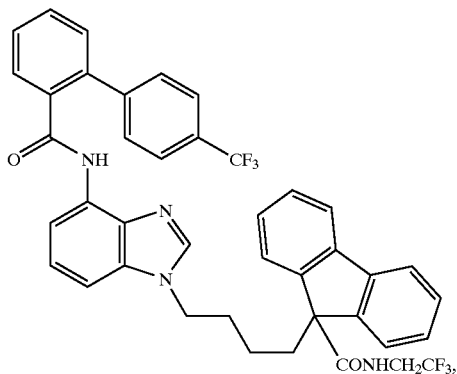

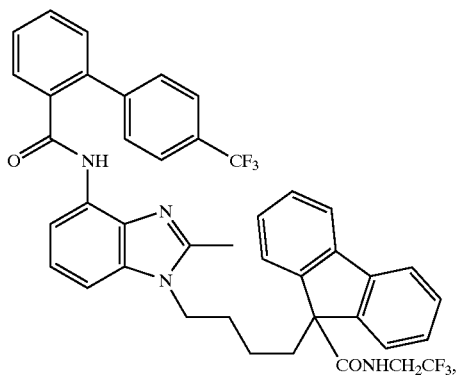

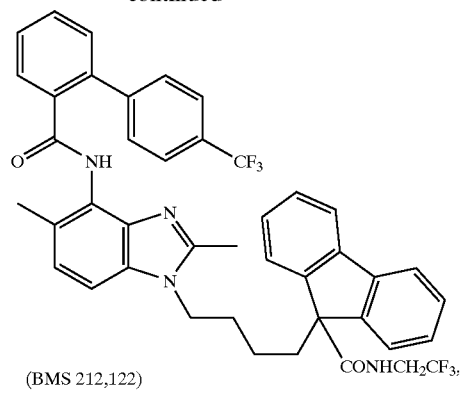

(BMS 212,122)

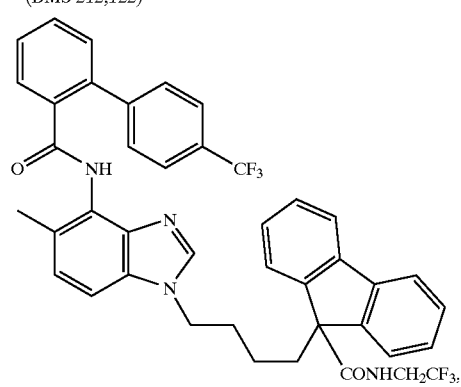

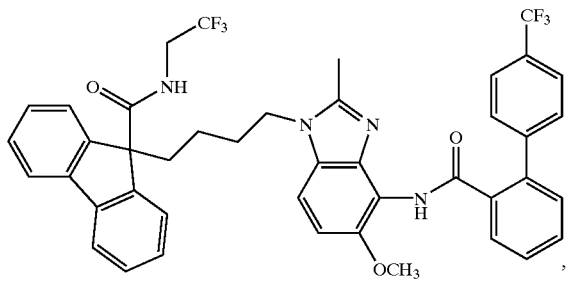

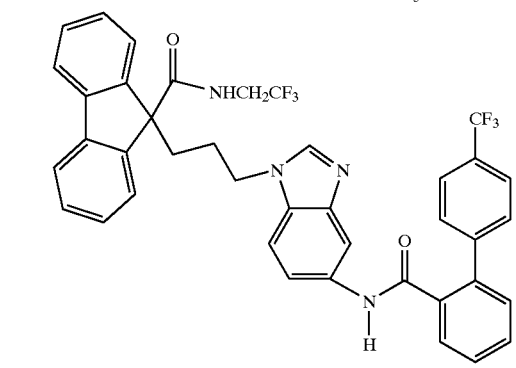

or a pharmaceutically acceptable salt thereof.

The squalene synthetase inhibitors suitable for use herein include, but are not limited to, α-phosphonosulfonates disclosed in U.S. application Ser. No. 08/266,888, Jul. 5, 1994, those disclosed by Biller et al, J. Med. Chem. 1988, Vol. 31, No. 10, pp 1869–1871, including isoprenoid (phosphinylmethyl)phosphonates such as those of the formula

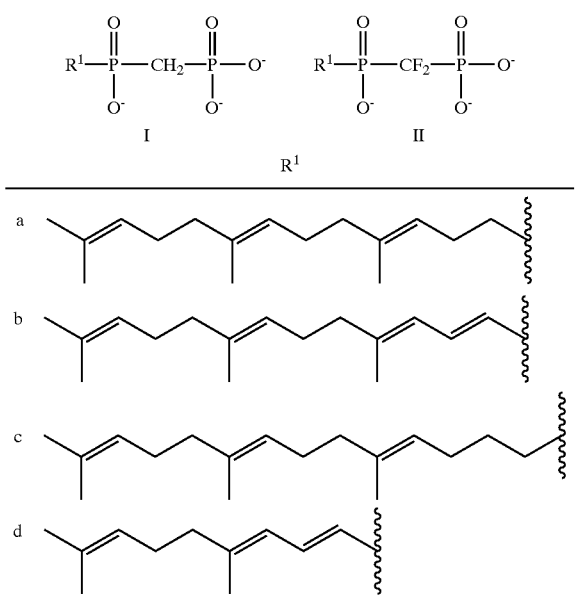

including the triacids thereof, triesters thereof and tripotassium and trisodium salts thereof as well as other squalene synthetase inhibitors disclosed in U.S. Pat. Nos. 4,871,721 and 4,924,024 and in Biller et al, J. Med. Chem., 1988, Vol. 31, No. 10, pp 1869 to 1871.

In addition, other squalene synthetase inhibitors suitable for use herein include the terpenoid pyrophosphates disclosed by P. Ortiz de Montellano et al, J. Med. Chem.; 1977, 20, 243–249, the farnesyl diphosphate analog A and presqualene pyrophosphate (PSQ-PP) analogs as disclosed by Corey and Volante, J. Am. Chem. Soc. 1976, 98, 1291–1293, phosphinylphosphonates reported by McClard, R. W. et al, J.A.C.S., 1987, 109, 5544 and cyclopropanes reported by Capson, T. L., PhD dissertation, June, 1987, Dept. Med. Chem. U. of Utah, Abstract, Table of Contents, pp. 16, 17, 40–43, 48–51, Summary.

All of the above U.S. applications are incorporated herein by reference.

Other cholesterol lowering drugs suitable for use herein include, but are not limited to, antihyperlipoproteinemic agents such as fibric acid derivatives, such as fenofibrate, gemfibrozil, clofibrate, bezafibrate, ciprofibrate, clinofibrate and the like, probucol, and related compounds as disclosed in U.S. Pat. No. 3,674,836, probucol and gemfibrozil being preferred, bile acid sequestrants such as cholestyramine, colestipol and DEAE-Sephadex (Secholex®, Polidexide®), as well as clofibrate, lipostabil (Rhone-Poulenc), Eisai E-5050 (an N-substituted ethanolamine derivative), imanixil (HOE-402), tetrahydrolipstatin (THL), istigmastanylphosphorylcholine (SPC, Roche), aminocyclodextrin (Tanabe Seiyoku), Ajinomoto AJ-814 (azulene derivative), melinamide (Sumitomo), Sandoz 58-035, American Cyanamid CL-277,082 and CL-283,546 (disubstituted urea derivatives), nicotinic acid, acipimox, acifran, neomycin, p-aminosalicylic acid, aspirin, oly(diallylmethylamine) derivatives such as disclosed in U.S. Pat. No. 4,759,923, quaternary amine poly(diallyldimethylammonium chloride) and ionenes such as disclosed in U.S. Pat. No. 4,027,009, and other known serum cholesterol lowering agents.

Preferred combinations in accordance with the invention are clopidogrel and ifetroban and optionally pravastatin, atorvastatin, simvastatin, lovastatin, cerivastatin or fluvastatin.

In carrying out the method of the present invention, the ADP-receptor blocking antiplatelet drug in combination with the thromboxane $A_2$ receptor antagonist and optionally the cholesterol lowering drug may be administered to mammalian species, such as monkeys, dogs, cats, rats, humans, etc., and, as such, may be incorporated in a conventional systemic dosage form, such as a tablet, capsule, elixir or injectable. The above dosage forms will also include the necessary carrier material, excipient, lubricant, buffer, antibacterial, bulking agent (such as mennitol), anti-oxidants (ascorbic acid of sodium bisulfite) or the like. Oral dosage forms are preferred, although parenteral forms are quite satisfactory as well.

The dose administered must be carefully adjusted according to age, weight and condition of the patient, as well as the route of administration, dosage form and regimen and the desired result.

Clopidogrel will be employed in an oral daily dosage within the range from about 10 to about 1000 mg and preferably from about 25 to about 600 mg, and most preferably from about 50 to about 100 mg.

Ticlopidine may be employed in a daily dosage as set out in the 1997 PDR (250 mg) although daily dosages of from about 10 to about 1000 mg, preferably from about 25 to about 800 mg may be employed in accordance with the present invention.

The thromboxane $A_2$ receptor antagonist alone or in combination with one or more components of the combination of the invention may be incorporated in a conventional dosage form, such as a tablet, capsule, elixir, cream, suppository, aerosol spray or injectable. The above dosage forms will also include the necessary carrier material, excipient, lubricant, buffer, antibacterial, bulking agent (such as mannitol), antioxidants (ascorbic acid of sodium bisulfite) or the like. Oral dosage forms are preferred, although parenteral forms are quite satisfactory as well.

The thromboxane $A_2$ receptor antagonist may be employed in a separate dosage form from the ADP-receptor blocking antiplatelet drug and optional cholesterol lowering drug, such as separate injections and/or tablets or they may be employed in a single dosage form, such as a single injection and/or tablet.

With regard to such systemic formulations, where the thromboxane $A_2$ receptor antagonist is to be employed alone, single or divided doses of from about 0.1 to about 2500 mg preferably from about 2 to about 2000 mg, one to eight times daily, may be administered in systemic dosage forms as described above.

With regard to combinations of the thromboxane $A_2$ receptor antagonist with ADP-receptor blocking antiplatelet drug, and optional cholesterol lowering drug, single or divided doses of from 0.1 to about 2500 mg of thromboxane $A_2$ receptor antagonist, preferably 2 to 2000 mg thromboxane $A_2$ receptor antagonist, and from about 2 to about 2000 mg ADP-receptor blocking antiplatelet drug and preferably from about 5 to about 1500 mg ADP-receptor blocking antiplatelet drug may be administered one to eight times daily.

With regard to the optional cholesterol lowering drug, for oral administration, a satisfactory result my be obtained employing the HMG CoA reductase inhibitor in dosages employed, for example, for pravastatin, simvastatin, fluvastatin, lovastatin, atorvastatin or cerivastatin, as indicated in the Physician's Desk Reference, such as in an amount within the range of from about 1 to 2000 mg, and preferably from about 4 to about 200 mg.

For oral administration, a satisfactory result may be obtained employing the optional MTP inhibitor in an amount within the range of from about 0.01 mg/kg to about 100 mg/kg and preferably from about 0.1 mg/kg to about 75 mg/kg.

A preferred oral dosage form, such as tablets or capsules, will contain the MTP inhibitor in an amount of from about 5 to about 500 mg, preferably from about 10 to about 400 mg, and more preferably from about 20 to about 250 mg.

For parenteral administration, the MTP inhibitor will be employed in an amount within the range of from about 0.005 mg/kg to about 10 mg/kg and preferably from about 0.005 mg/kg to about 8 mg/kg.

The optional squalene synthetase inhibitor may be employed in dosages in an amount within the range of from about 10 mg to about 2000 mg and preferably from about 25 mg to about 200 mg.

A preferred oral dosage form, such as tablets or capsules, will contain clopidogrel or ticlopidine in an amount of from about 10 to about 500 mg, the thromboxane $A_2$ receptor antagonist in an amount from about 1 to about 1500 mg, preferably from about 2 to about 100 mg, the optional HMG CoA reductase inhibitor in an amount of from about 0.1 to about 100 mg, preferably from about 5 to about 80 mg, and more preferably from about 10 to about 50 mg, and/or the optional MTP inhibitor in an amount from about 10 to about 400 mg.

The optional cholesterol lowering drugs when present will be employed in dosages normally employed as indicated in the Physician's Desk Reference, for each of such agents such as in an amount within the range of from about 2 mg to about 7500 mg and preferably from about 2 mg to about 4000 mg.

Aspirin may also be optionally present and may be employed in daily dosages within the range from about 20 mg to about 5000 mg, preferably from about 40 mg to about 500 mg, and in a weight ratio to the ADP-receptor blocking antiplatelet drug within the range from about 50:1 to about 0.5:1, preferably from about 25:1 to about 1:1.

The ADP-receptor blocking antiplatelet drug, thromboxane $A_2$ receptor antagonist and the optional cholesterol lowering agent and optionally aspirin may be employed together in the same oral dosage form or in separate oral dosage forms taken at the same time.

The compositions described above may be administered in the dosage forms as described above in single or divided doses of one to four times daily. It may be advisable to start a patient on a low dose combination and work up gradually to a high dose combination.

Tablets of various sizes can be prepared, e.g., of about 2 to 2000 mg in total weight, containing one or both of the active substances in the ranges described above, with the remainder being a physiologically acceptable carrier of other materials according to accepted pharmaceutical practice. These tablets can, of course, be scored to provide for fractional doses. Gelatin capsules can be similarly formulated.

Liquid formulations can also be prepared by dissolving or suspending one or the combination of active substances in a conventional liquid vehicle acceptable for pharmaceutical administration so as to provide the desired dosage in one to four teaspoonsful.

Such dosage forms can be administered to the patient on a regimen of one to four doses per day.

According to another modification, in order to more finely regulate the dosage schedule, the active substances may be administered separately in individual dosage units at the same time or carefully coordinated times. Since blood levels are built up and maintained by a regulated schedule of administration, the same result is achieved by the simultaneous presence of the two substances. The respective substances can be individually formulated in separate unit dosage forms in a manner similar to that described above.

Fixed combinations of the ADP-receptor blocking antiplatelet drug, thromboxane $A_2$ receptor antagonist and optional cholesterol lowering drug and optionally aspirin are more convenient and are preferred, especially in tablet or capsule form for oral administration.

In formulating the compositions, the active substances, in the amounts described above, are compounded according to accepted pharmaceutical practice with a physiologically acceptable vehicle, carrier, excipient, binder, preservative, stabilizer, flavor, etc., in the particular type of unit dosage form.

Illustrative of the adjuvants which may be incorporated in tablets are the following: a binder such as gum tragacanth, acacia, corn starch or gelatin; an excipient such as dicalcium phosphate or cellulose; a disintegrating agent such as corn starch, potato starch, alginic acid or the like; a lubricant such as stearic acid or magnesium stearate; a sweetening agent such as sucrose, aspartame, lactose or saccharin; a flavoring agent such as orange, peppermint, oil of wintergreen or cherry. When the dosage unit form is a capsule, it may contain in addition to materials of the above type a liquid carrier such as a fatty oil. Various other materials may be present as coatings or to otherwise modify the physical form of the dosage unit. For instance, tablets or capsules may be coated with shellac, sugar or both. A syrup of elixir may contain the active compound, water, alcohol or the like as the carrier, glycerol as solubilizer, sucrose as sweetening agent, methyl and propyl parabens as preservatives, a dye and a flavoring such as cherry or orange.

Some of the active substances described above form commonly known, pharmaceutically acceptable salts such as alkali metal and other common basic salts or acid addition salts, etc. References to the base substances are therefore intended to include those common salts known to be substantially equivalent to the parent compound.

The formulations as described above will be administered for a prolonged period, that is, for as long as the potential for acute coronary syndrome, including myocardial infarction, stable or unstable angina, reocclusion after PTCA, restenosis after PTCA, as well as intermittent claudication, TIA, stroke and reversible ischemia neurological deficit remains or the symptoms continue. Sustained release forms of such formulations which may provide such amounts biweekly, weekly, monthly and the like may also be employed. A dosing period of at least one to two weeks are required to achieve minimal benefit.

The following Examples represent preferred embodiments of the present invention.

Formulations suitable for oral administration for inhibiting platelet aggregation and thrombus formation are prepared as described below.

EXAMPLES 1

Capsules are prepared each containing about 98 mg clopidogrel (as described below) and 35 mg ifetroban.

| Ingredient | Example 1 Amount (mg/Capsule) |
| --- | --- |
| Clopidogrel hydrogen sulfate | 98 |
| Lactose, Hydrous, NF ca. | 108 ca. |
| Microcrystalline Cellulose, NF ca. | 13 |
| Pregelatinized Starch, NF | 10.5 |
| Polyethylene glycol 6000 NF | 7.5 |
| Hydrogenated castor oil, NF | 3.3 |

The above clopidogrel tablet is prepared by blending anhydrous lactose, clopidogrel hydrogen sulfate, pregelatinized starch, polyethylene glycol 6000 in a bin-type blender for about 15 minutes at 7 rpm.

The blended mix is then screened (1.25 mm screen) and blended for about 30 minutes at 7 rpm in a bin-type blender. The blend is compacted using a roller compactor fitted with milling equipment. The milled granulation which contains particles ranging from 1 mm to less than 20 mm is blended with microcrystalline cellulose (screen through 1.25 mm screen) and hydrogenated castor oil in a bin-type blender for about 30 minutes at 7 rpm. The blend is compressed into 240 mg tablets.

A formulation containing the sodium salt of ifetroban, in the form of tablets, having the following composition, was prepared by the direct compression manufacturing process as described in U.S. Pat. No. 5,506,248 which is incorporated herein by reference.

| Ingredient | Percent by Weight |
| --- | --- |
| Na Salt of Ifetroban | 35 |
| Mannitol | 50 |
| Microcrystalline Cellulose | 8 |
| Crospovidone | 3.0 |
| Magnesium Oxide | 2.0 |
| Magnesium Stearate | 1.5 |
| Colloidal Silica | 0.3 |

Na salt of ifetroban, magnesium oxide, mannitol, microcrystalline cellulose, and crospovidone were mixed together for 2 to 10 minutes employing a suitable mixer. The resulting mixture was passed through a #12 to #40 mesh size screen. Thereafter, magnesium stearate and colloidal silica were added and mixing was continued for 1 to 3 minutes.

The resulting homogeneous mixture was then compressed into tablets each containing 35 mg, ifetroban sodium salt.

The clopidogrel tablets and ifetroban tablets are ground into powders and filled into a single capsule.

EXAMPLE 2

Capsules each containing 250 mg ticlopidine (tablets as described in 1997 PDR) or 98 mg clopidogrel (Example 1) 35 mg ifetroban tablets (as described in Example 1), and optionally 40 mg pravastatin (tablets as described in 1997 PDR) are prepared by grinding up the ticlopidine tablet, and ifetroban tablet, and optionally the pravastatin tablet and filling the resulting powders into a single capsule.

EXAMPLE 3 AND 4

Clopidogrel tablets (25 mg, 50 mg or 98 mg) or ticlopidine tablets (250 mg) and ifetroban tablets (5.25 mg 10 mg and 20 mg as per U.S. Pat. No. 5,506,248) and optionally pravastatin tablets (10, 20 or 40 mg as described in the 1997 PDR) may be administered as a combination in accordance with the teachings of the present invention to inhibit platelet aggregation and thrombus formulation. In addition, the clopidogrel and ifetroban and optionally pravastatin tablets may be ground up into powders and used together in a single capsule.

EXAMPLE 5

The following experiment was carried out to demonstrate inhibition of vessel injury-induced venous thrombosis by clopidogrel plus ifetroban in relation to antiplatelet activity.

The risk of pulmonary embolism after orthopedic surgery represents an unmet medical need. Clopidogrel was tested in the $FeCl_2$ model to establish its potential therapeutic utility. In these experiments ex vivo indices of platelet activation were determined to correlate antithrombotic and antiplatelet activities. The antiplatelet agent ifetroban, which acts by blockade of thromboxane receptors, was also tested. In addition, antithrombotic efficacy of the combination of treatments with clopidogrel and ifetroban was evaluated.

Methods

Thrombosis Procedure. Male Sprague Dawley rats (350–450 g) were anesthetized with sodium pentobarbital (50 mg/kg i.p.). A jugular vein was cannulated for drug infusion or anesthetic supplementation, and the trachea was intubated to ensure airway patency. The vena cava was isolated by a midline abdominal incision and cleared of connective tissue. A fiberoptic probe (model P-433-10, 0.8 mm tip diameter) was placed on the dorsal surface of the vena cava distal to the renal veins and attached to a laser doppler blood perfusion monitor (model BPM 430-2, Vasamedics, St. Paul, Minn.). When baseline flow had stabilized, a 2 mm×5 mm strip of filter paper was saturated in 15% $FeCl_2$ and placed on the vena cava downstream from the flow probe for 1 min. The vena cava was dissected free 60 min after filter paper application and opened lengthwise. The thrombus was removed to determine wet and dry thrombus weights on a Sartorius R-160P balance (Brinkmann Instruments Inc., Westbury, N.Y.). Blood flow was monitored on an R-611 physiological recorder (Sensor Medics, Anaheim, Calif.). Total blood flow was calculated by planimetry and normalized as percent of baseline flow (0 min=100%) over 60 min.

Ex Vivo Platelet Function and Coagulation Testing. Male Sprague Dawley rats (350–450 g) were anesthetized with sodium pentobarbital (50 mg/kg i.p.) The vena cava was isolated by a midline abdominal incision and 5 to 8 ml of blood was withdrawn into a $\frac{1}{10}^{th}$ volume of 3.8% Na citrate. A portion of each blood sample was centrifuged for 3 sec in a Microcentrifuge E (Beckman, Palo Alto, Calif., USA) to prepare platelet rich plasma (PRP) and for 3 min to prepare platelet poor plasma (PPP). The PRP was adjusted to a count of ~450×$10^3$ platelets per gl by adding PPP.

Platelet aggregation responses of PRP to ADP (1,3 and 10 $\mu$M; Chrono-Log Corp., Havertown, Pa., USA) were determined using the photometric technique described for a model 540 aggregometer (Chrono-Log Corp.).

A modified activated clotting time (ACT) was determined in a BBL Fibrometer (Becton Dickinson, Cockeysville, Md., USA) by incubating blood (100 gl) with celite (30 $\mu$l of 1% celite suspension +70 $\mu$l saline) for 3 min at 37° C. and recalcifying (100 $\mu$l of 20 mM $CaCl_2$). Celite (Haemoscope, Skokie, Ill., USA) is a contact activator used to shorten control clotting times in plastic reaction vessels. The development of clot tensile strength as a function of time was determined in a model 3000 computerized thrombelastograph (Haemoscope) by activating 284 µl of whole blood with 28 µl of 1% celite suspension and 18 µl of 150 mM $CaCl_2$.

Drug treatments. There were 3 separate studies. In the first study rats were dosed once daily for 3 days with an oral gavage of either saline (n=6) or clopidogrel 3 (n=5), 10 (n=5), 20 (n=4) mg/kg). One hour after the last dose, rats were anethetized for the thrombosis protocol or blood was obtained for ex vivo testing of platelet function and whole blood coagulation. In the second study a continuous i.v. infusion of either saline or ifetroban (150 µg/kg/min) was administered starting 15 min before $FeCl_2$-induced injury of the vena cava. In the third study, rats were treated with saline or clopidogrel (2 mg/kg per day for 3 days) and administered either saline or ifetroban (150 µg/kg/min) starting 15 min before $FeCl_2$ application.

Results

The benefit of prophylactic clopidogrel treatment on vessel injury-induced venous thrombosis was characterized by a reduction in thrombus weight and improvement in vessel patency and blood flow. Thrombus weight was decreased by 46, 72, and 84% at clopidogrel doses of 3, 10 and 20 mg/kg daily for 3 days, respectively. In contrast, ifetroban was inactive in this model even though the dose used had been shown previously to block $\geq 99\%$ of rat platelet thromboxane $A_2$ receptors (Schumacher et al., J. Cardiovasc. Pharmacol., 22:526–533, 1993). Doses of clopidogrel which were antithrombotic inhibited ex vivo platelet aggregation responses to ADP. This result was dependent on both the dose of clopidogrel and the concentration of ADP. In vehicle-treated rats, threshold maximal aggregation was achieved with 3 µM ADP, and the 10-mg/kg dose of clopidogrel inhibited this activity by 50%. A near maximal 86% inhibition of ADP-induced aggregation was achieved with the 20-mg/kg clopidogrel dose. However, the platelet shape change response to ADP was unaffected by even this high dose of clopidogrel. The ex vivo whole blood coagulation tests were also unaffected by clopidogrel.

In rats, the clopidogrel dose (2 mg/kg per day for 3 days). was not sufficient to inhibit thrombus formation, and ifetroban alone produced no significant effect. However, the combination of clopidogrel pretreatment plus acute ifetroban treatment significantly reduced thrombus weight by 43%. The ratio of dry to wet thrombus weights did not differ among treatment groups and averaged 0.27±0.003.

Discussion

Clopidogrel is well recognized as a potent inhibitor of ADP-induced platelet aggregation in humans and rats. Clopidogrel has produced dose-dependent activity in rat models of carotid artery thrombosis induced by transmural vessel injury and vena cava thrombosis induced by either transmural vessel injury or partial stasis of blood flow combined with mild vessel injury. These models are reminders of the inadequacy of current anticoagulant therapy in situations where thrombosis is complicated by severe vessel injury, especially venous thrombosis accompanying orthopedic surgery. Potent inhibition ($\geq 75\%$) of stasis-induced vena cava thrombosis was achieved using doses of heparin and a low-molecular-weight heparin (fragmin) which increased APTT by only 1.8-fold, and using a dose of warfarin which produced a PT ratio (INR) of 2.2. These results are consistent with the well established effectiveness of these indirect thrombin inhibitors in settings of uncomplicated venous thrombosis. In contrast, comparable inhibition of vessel injury-induced venous thrombosis necessitated higher doses which caused APTT increases of >10-fold (heparin) and 6.6-fold (fragmin) and an INR of 9.5 (warfarin). Inhibition of platelet-dependent carotid artery thrombosis by these drugs also required higher doses exerting equal or greater effects on blood coagulation (Schumacher et al., J. Cardiovasc. Pharmacol., 28:19–25, 1996).

The dose-dependent antithrombotic activity of clopidogrel in each of the thrombosis models was as follows. Unlike the indirect thrombin inhibitors, clopidogrel was least effective against stasis-induced venous thrombosis. This profile would be expected for an antiplatelet drug, because the model is not considered to be platelet-dependent. It is the near equivalent efficacy of clopidogrel against vessel injury-induced venous and arterial thrombosis that was unexpected. The 10-mg/kg dose of clopidogrel showed good activity in all three models. The potential uniqueness of clopidogrel is further underscored by the failure of both ifetroban and aspirin (Schumacher et al., 1993a, Schumacher and Steinbacher, J. Cardiovasc. Pharmacol. 22:526–533, 1993) in the vessel injury-induced venous thrombosis model.

In order to compare clopidogrel doses that were effective in experimental venous thrombosis to the dose used in clinical studies, platelet aggregation was used as an ex vivo indicator of pharmacodynamic activity. Clopidogrel exerted significant inhibition of both venous and arterial thrombosis at a dose causing 50% inhibition of ex vivo platelet function. Clinical studies have demonstrated the efficacy of clopidogrel against arterial thrombosis at a dose that inhibits human platelet aggregation to 5 µM ADP by 40 to 50%. Although ifetroban alone was effective in the uncomplicated venous thrombosis model, in the vessel injury induced venous thrombosis model it was not effective. This suggests that the thromboxane mechanism does not play the key role in platelet involvement in this platelet-dependent model. Aspirin, which also inhibits the thromboxane mechanism, was inactive in both venous thrombosis models. The activity of clopidogrel in these models implicates the ADP receptor as an initiating platelet receptor mechanism in thrombogenesis involving low shear forces, vessel injury and the development of platelet-poor thrombi.

Clopidogrel has not been reported to affect coagulation in classical clotting tests that use plasma that is devoid of platelets. This suggests that the mechanism whereby clopidogrel inhibits venous thrombosis is probably related to platelet inhibition separate from a direct action on in vitro blood coagulation.

The efficacy of ifetroban in animals treated with a sub-threshold dose of clopidogrel is particularly surprising. Clopidogrel and ifetroban show synergistic antiplatelet activity. They act by antagonizing separate receptor-mediated mechanisms of platelet aggregation: clopidogrel blocks ADP-induced platelet aggregation, and ifetroban antagonizes thromboxane receptor dependent platelet activation. These mechanisms represent two of the three most important pathways for recruitment of platelets into growing thrombi; thrombin receptor activation is the third key platelet pathway that is not blocked effectively by either clopidogrel or ifetroban. The synergistic efficacy of clopidogrel and ifetroban in this model of vessel-injury induced venous thrombosis attests to the pivotal role of platelets in the model. Clearly, high doses of clopidogrel are optimally effective in this model, but it may not be practical to use such high doses in patients. These results suggest that optimal efficacy might be achieved with moderate doses of clopidogrel plus ifetroban. One potential mechanism for the synergistic activity of clopidogrel and ifetroban in this model involves the role of activated platelets as a platform for thrombin generation.

CONCLUSIONS

Clopidogrel is a potent inhibitor of ADP-induced aggregation with well-established utility in experimental arterial thrombosis; however, its effectiveness against venous thrombosis is less well understood. The thromboxane receptor antagonist, ifetroban, also produced intermediate efficacy in this model. In contrast, inhibition of vena cava thrombosis induced by topical application of FeCl2 requires super-therapeutic doses of anticoagulants and is more representative of platelet-dependent venous thrombosis complicated by severe vessel injury during major knee and hip surgery. Clopidogrel and ifetroban were tested in this rat model of vessel injury-induced thrombosis. Clopidogrel, dosed orally once daily for 3 days at 3, 10 and 20 mg/kg, inhibited acute thrombus formation by 46, 72, and 84%, respectively. At 2 mg/kg clopidogrel had no effect on thrombus formation. In vehicle-treated rats, 3 $\mu$M ADP caused threshold maximal platelet aggregation, and the 10-mg/kg clopidogrel dose inhibited this activity by 50%, which is in the activity range of the clinical dose. Ifetroban (and aspirin in previous experiments) failed to inhibit thrombosis in this model. However, the combination of ifetroban and the sub-threshold dose of clopidogrel (2 mg/kg) reduced thrombus formation by 43% (p<0.01). Thus, ifetroban and clopidogrel may appear to produce synergistic antithrombotic activity.

What is claimed is:

1. A pharmaceutical synergistic combination consisting essentially of an ADP-receptor blocking antiplatelet drug which is clopidogrel and a thromboxane $A_2$ receptor antagonist which is ifetroban.

2. The combination as defined in claim 1 wherein the antiplatelet drug is employed in a weight ratio to the thromboxane $A_2$ receptor antagonist within the range of from about 0.001:1 to about 1000:1.

3. A method for preventing or inhibiting platelet aggregation and/or thrombus formation in a mammalian species, which comprises administering to a patient in need of said treatment a therapeutically effective amount of a pharmaceutical synergistic combination as defined in claim 1.

* * * * *